US012186571B2

(12) United States Patent
Cao et al.

(10) Patent No.: US 12,186,571 B2
(45) Date of Patent: *Jan. 7, 2025

(54) MULTI-THRESHOLD SENSING OF CARDIAC ELECTRICAL SIGNALS IN AN IMPLANTABLE MEDICAL DEVICE

(71) Applicant: Medtronic, Inc., Minneapolis, MN (US)

(72) Inventors: Jian Cao, Shoreview, MN (US); Gerald P. Arne, Wayzata, MN (US); Timothy A. Ebeling, Circle Pines, MN (US); Yanina Grinberg, Plymouth, MN (US); Michael W. Heinks, New Brighton, MN (US); Paul R. Solheim, Blaine, MN (US); Xusheng Zhang, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 114 days.

This patent is subject to a terminal disclaimer.

(21) Appl. No.: 18/069,218

(22) Filed: Dec. 20, 2022

(65) Prior Publication Data
US 2023/0129026 A1     Apr. 27, 2023

Related U.S. Application Data

(63) Continuation of application No. 17/068,011, filed on Oct. 12, 2020, now Pat. No. 11,547,864, which is a continuation of application No. 15/790,255, filed on Oct. 23, 2017, now Pat. No. 10,799,710.

(51) Int. Cl.
*A61N 1/39*     (2006.01)
*A61N 1/362*     (2006.01)
*A61N 1/365*     (2006.01)
*A61N 1/372*     (2006.01)
(Continued)

(52) U.S. Cl.
CPC ......... *A61N 1/3956* (2013.01); *A61N 1/3621* (2013.01); *A61N 1/3622* (2013.01); *A61N 1/365* (2013.01); *A61N 1/37252* (2013.01); *A61B 5/352* (2021.01); *A61N 1/05* (2013.01); *A61N 1/3931* (2013.01); *A61N 1/3943* (2013.01); *A61N 1/3987* (2013.01)

(58) Field of Classification Search
CPC .................................................. A61N 1/3956
See application file for complete search history.

(56) References Cited

U.S. PATENT DOCUMENTS

| | | |
|---|---|---|
| 5,312,441 A | 5/1994 | Mader et al. |
| 5,354,316 A | 10/1994 | Keimel |
| 5,545,186 A | 8/1996 | Olson et al. |

(Continued)

OTHER PUBLICATIONS

Swerdlow et al., "Advanced ICD Troubleshoooting: Part I", PACE, Dec. 2005; vol. 28, 25 pages.

(Continued)

*Primary Examiner* — Alyssa M Alter

(57) ABSTRACT

An implantable medical device system is configured to sense cardiac events in response to a cardiac electrical signal crossing a cardiac event sensing threshold. A control circuit is configured to determine a drop time interval based on a heart rate and control a sensing circuit to hold the cardiac event sensing threshold at a threshold value during the drop time interval.

20 Claims, 19 Drawing Sheets

(51) Int. Cl.
    *A61B 5/352*         (2021.01)
    *A61N 1/05*          (2006.01)

(56) References Cited

U.S. PATENT DOCUMENTS

| | | | |
|---|---|---|---|
| 5,620,466 | A | 4/1997 | Haefner et al. |
| 5,709,215 | A | 1/1998 | Perttu et al. |
| 5,800,466 | A | 9/1998 | Routh et al. |
| 5,957,857 | A | 9/1999 | Hartley |
| 6,249,701 | B1 | 6/2001 | Rajasekhar et al. |
| 6,393,316 | B1 | 5/2002 | Gillberg et al. |
| 6,459,937 | B1 | 10/2002 | Morgan et al. |
| 6,526,311 | B2 | 2/2003 | Begemann |
| 6,539,259 | B1 | 3/2003 | Weinberg et al. |
| 6,862,476 | B2 | 3/2005 | Mouchawar et al. |
| 7,027,858 | B2 | 4/2006 | Cao et al. |
| 7,031,771 | B2 | 4/2006 | Brown et al. |
| 7,330,757 | B2 | 2/2008 | Ostroff et al. |
| 7,333,855 | B2 | 2/2008 | Gunderson et al. |
| 7,444,182 | B2 | 10/2008 | Ostroff et al. |
| 7,496,409 | B2 | 2/2009 | Greenhut et al. |
| 7,761,150 | B2 | 7/2010 | Ghanem et al. |
| 7,783,354 | B2 | 8/2010 | Gunderson |
| 7,831,304 | B2 | 11/2010 | Cao et al. |
| 7,937,135 | B2 | 5/2011 | Ghanem et al. |
| 7,970,473 | B2 | 6/2011 | Nabutovsky et al. |
| 8,050,754 | B2 | 11/2011 | Ostroff et al. |
| 8,055,342 | B2 | 11/2011 | Zhang et al. |
| 8,160,684 | B2 | 4/2012 | Ghanem et al. |
| 8,386,024 | B2 | 2/2013 | Gunderson et al. |
| 8,437,842 | B2 | 5/2013 | Zhang et al. |
| 8,626,280 | B2 | 1/2014 | Allavatam et al. |
| 8,694,097 | B2 | 4/2014 | Cao et al. |
| 8,744,555 | B2 | 6/2014 | Allavatam et al. |
| 8,886,296 | B2 | 11/2014 | Patel |
| 8,914,106 | B2 | 12/2014 | Charlton et al. |
| 8,942,795 | B2 | 1/2015 | Gunderson et al. |
| 8,942,802 | B2 | 1/2015 | Ostroff et al. |
| 8,965,491 | B2 | 2/2015 | Allavatam et al. |
| 8,983,586 | B2 | 3/2015 | Zhang |
| 9,002,443 | B2 | 4/2015 | Zhang et al. |
| 9,155,485 | B2 | 10/2015 | Ostroff et al. |
| 9,561,005 | B2 | 2/2017 | Zhang |
| 9,597,525 | B2 | 3/2017 | Cao et al. |
| 10,799,710 | B2 * | 10/2020 | Cao .................. A61N 1/3621 |
| 11,547,864 | B2 * | 1/2023 | Cao .................. A61N 1/3956 |
| 2004/0049120 | A1 | 3/2004 | Cao et al. |
| 2012/0109240 | A1 | 5/2012 | Zhou et al. |
| 2015/0105680 | A1 | 4/2015 | Ostroff et al. |
| 2015/0306375 | A1 | 10/2015 | Marshall et al. |
| 2015/0306410 | A1 | 10/2015 | Marshall et al. |
| 2016/0001090 | A1 | 1/2016 | Ostroff et al. |
| 2016/0045129 | A1 | 2/2016 | Allavatam |
| 2016/0106989 | A1 | 4/2016 | Stadler et al. |
| 2016/0106991 | A1 | 4/2016 | Stadler et al. |

OTHER PUBLICATIONS

Zhang, et al., "System and Method for Sensing and Detection in an Extra-Cardiovascular Implantable Cardioverter Defibrillator", U.S. Appl. No. 15/140,802, filed Apr. 28, 2016, 77 pages.

(PCT/US2018/056967) PCT Notification of Transmittal of the International Search Report and the Written Opinion of the International Searching Authority, dated Jan. 25, 2019, 10 pages.

European Communication dated May 12, 2023, European Patent Application No. 23156009.5, 8 pages.

* cited by examiner

MULTI-THRESHOLD SENSING OF CARDIAC ELECTRICAL SIGNALS IN AN IMPLANTABLE MEDICAL DEVICE

CROSS-REFERENCE TO RELATED APPLICATIONS

This application is a continuation of U.S. patent application Ser. No. 17/068,011, filed Oct. 12, 2020, which is a continuation of U.S. patent application Ser. No. 15/790,255 filed Oct. 23, 2017 (granted as U.S. Pat. No. 10,799,710), the entire contents of which is incorporated by reference herein.

TECHNICAL FIELD

The disclosure relates generally to an implantable medical device system and method for controlling a threshold used for sensing cardiac electrical events from a cardiac electrical signal.

BACKGROUND

Medical devices, such as cardiac pacemakers and implantable cardioverter defibrillators (ICDs), provide therapeutic electrical stimulation to a heart of a patient via electrodes carried by one or more medical electrical leads and/or a housing of the medical device. The electrical stimulation may include signals such as pacing pulses or cardioversion or defibrillation shocks. The medical device may sense cardiac electrical signals attendant to the intrinsic depolarizations of the heart and control delivery of stimulation signals to the heart based on sensed cardiac electrical signals. Upon detection of an abnormal rhythm, such as bradycardia, tachycardia or fibrillation, an appropriate electrical stimulation therapy may be delivered to restore or maintain a more normal rhythm of the heart. For example, an ICD may deliver pacing pulses to the heart of the patient upon detecting bradycardia or tachycardia or deliver cardioversion or defibrillation shocks to the heart upon detecting tachycardia or fibrillation.

SUMMARY

In general, the disclosure is directed to techniques for controlling a cardiac event sensing threshold by a medical device. The cardiac event sensing threshold may be an R-wave sensing threshold controlled by the medical device to avoid oversensing of T-waves and P-waves while maintaining high sensitivity for detecting abnormal rhythms, such as atrial or ventricular tachyarrhythmias. The cardiac event sensing threshold is held at a threshold value during a drop time interval that is set based on a heart rate interval, which may be a pacing interval or a sensed event interval. For example, the drop time interval may be set to a percentage of the pacing interval. The medical device may be an ICD coupled to an extra-cardiovascular lead carrying at least one sensing electrode in some examples.

In one example, the disclosure provides a system comprising an implantable medical device for sensing cardiac electrical events. The system includes a sensing circuit, a therapy delivery circuit and a control circuit. The sensing circuit is configured to receive a cardiac electrical signal from a patient's heart and sense a cardiac event attendant to a myocardial depolarization in response to the cardiac electrical signal crossing a cardiac event sensing threshold. The therapy delivery circuit is configured to deliver an electrical stimulation therapy to a patient's heart. The control circuit is configured to determine a drop time interval based on a heart rate, control the sensing circuit to hold the cardiac event sensing threshold at a predetermined threshold value until an expiration of the drop time interval, determine a need for an electrical stimulation therapy based on a rate of cardiac events sensed by the sensing circuit, and control the therapy delivery circuit to deliver an electrical stimulation pulse in response to determining the need for the electrical stimulation therapy.

In another example, the disclosure provides a method performed by a system including an implantable medical device for sensing cardiac electrical signals. The method includes receiving a cardiac electrical signal from a patient's heart, sensing a cardiac event attendant to a myocardial depolarization in response to the cardiac electrical signal crossing a cardiac event sensing threshold, the cardiac event sensing threshold being adjusted from a first threshold value to a second threshold value upon expiration of a drop time interval, determining a need for an electrical stimulation therapy based on a rate of cardiac events, and delivering an electrical stimulation pulse in response to determining the need for the electrical stimulation therapy.

In another example, the disclosure provides a non-transitory, computer-readable storage medium comprising a set of instructions which, when executed by processor of an implantable medical device system, cause the system to receive a cardiac electrical signal from a patient's heart by a sensing circuit of the implantable medical device, sense a cardiac event attendant to a myocardial depolarization in response to the cardiac electrical signal crossing a cardiac event sensing threshold, determine whether a need for an electrical stimulation therapy exists based on a rate of cardiac events sensed by the sensing circuit, and control a therapy delivery circuit of the implantable medical device to deliver an electrical stimulation pulse in response to determining that the need for the electrical stimulation therapy exists. Sensing the cardiac event includes determining a drop time interval based on a heart rate and controlling the sensing circuit to hold the cardiac event sensing threshold at a predetermined threshold value until an expiration the drop time interval.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for sensing cardiac electrical signals by an implantable medical device (IMD) using a multi-level cardiac event sensing threshold. The multi-level cardiac event sensing threshold is set by a sensing circuit of the IMD under the control of a control circuit and is adjusted between threshold value levels at determined time intervals. When a cardiac electrical signal received by the sensing circuit crosses the cardiac event sensing threshold, a cardiac event is sensed. In some examples, the cardiac electrical signal is received by the IMD using implanted, extra-cardiovascular electrodes. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. The techniques disclosed herein provide a method for reliably sensing R-waves, attendant to ventricular depolarization, using extra-cardiovascular electrodes by applying multiple sensing thresholds to avoid oversensing of T-waves attendant to ventricular repolarization and P-waves attendant to atrial depolarization.

The techniques are described in conjunction with an implantable medical lead carrying extra-cardiovascular electrodes, but aspects disclosed herein may be utilized in conjunction with other cardiac electrical sensing lead and electrode systems. For example, the techniques for controlling a cardiac event sensing threshold as described in conjunction with the accompanying drawings may be implemented in any implantable or external medical device enabled for sensing cardiac electrical signals, including implantable pacemakers, ICDs or cardiac monitors coupled to transvenous or epicardial leads carrying sensing electrodes; leadless pacemakers, ICDs or cardiac monitors having housing-based sensing electrodes; and external or wearable pacemakers, defibrillators, or cardiac monitors coupled to external, surface or skin electrodes.

Figure 1A:
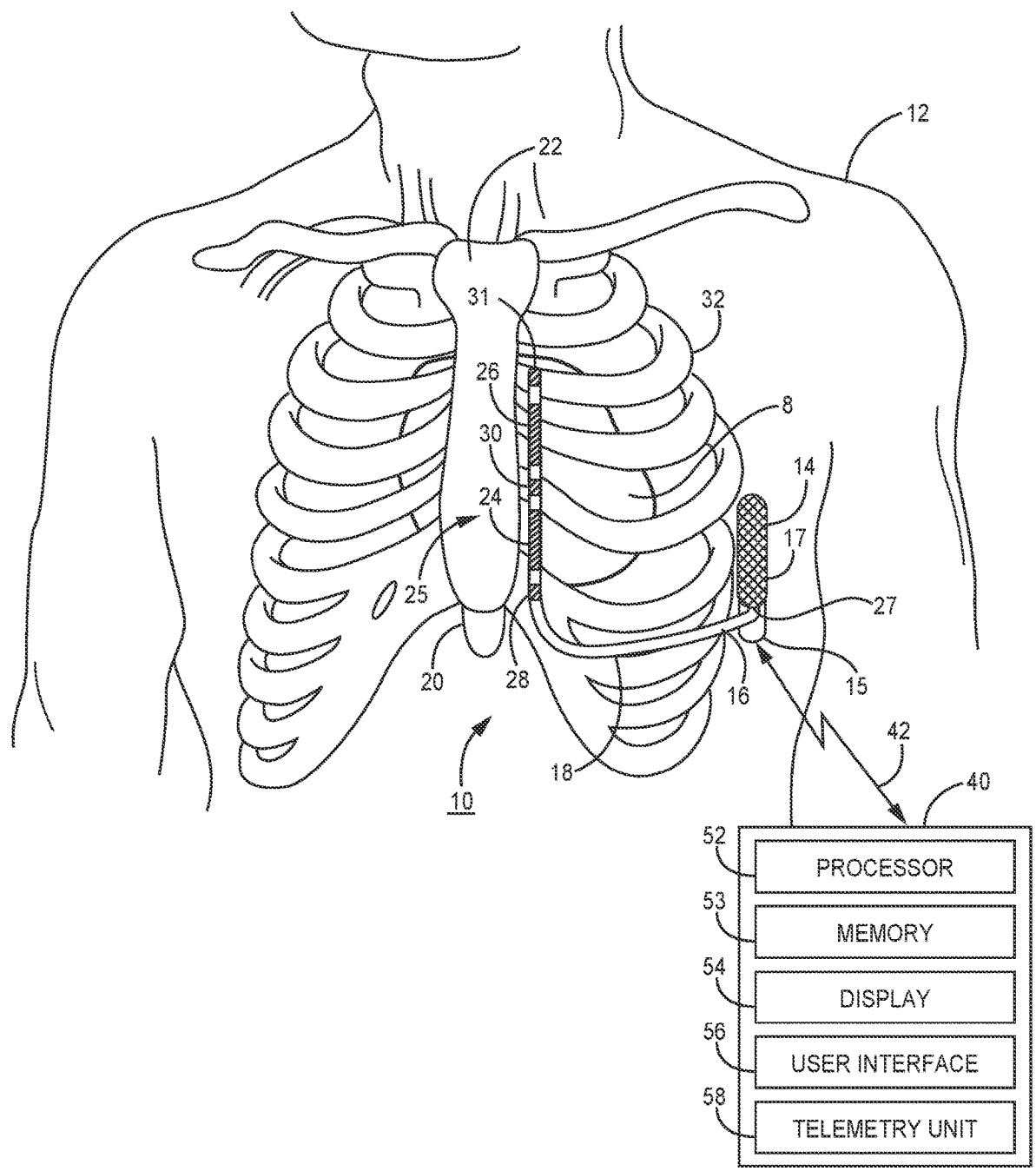
FIGS. 1A and 1B are conceptual diagrams of an extra-cardiovascular ICD system according to one example.
Figure 1B:
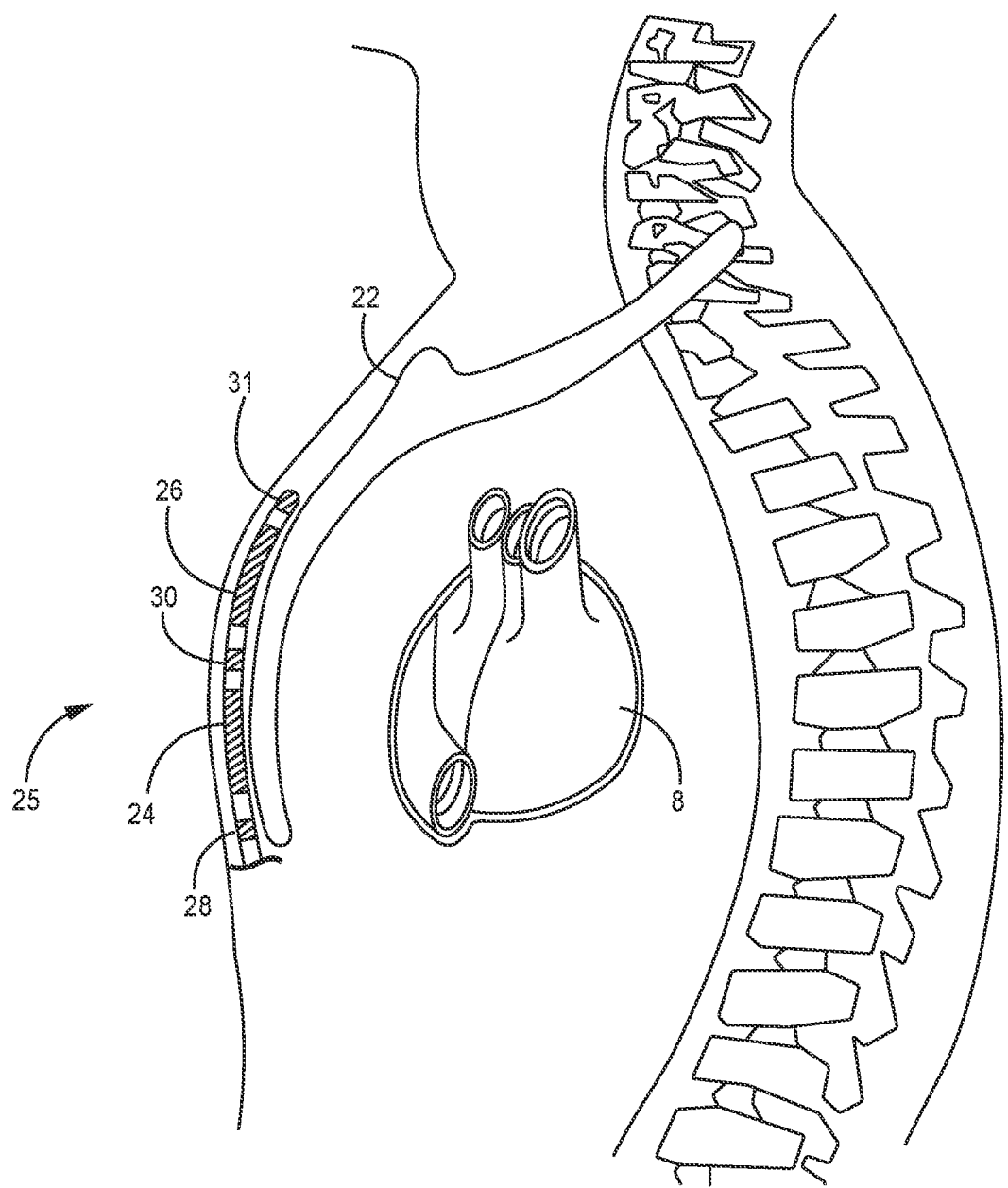

FIGS. 1A and 1B are conceptual diagrams of one example of an extra-cardiovascular ICD system 10 in which the presently disclosed techniques may be implemented. FIG. 1A is a front view of ICD system 10 implanted within patient 12. FIG. 1B is a side view of ICD system 10 implanted within patient 12. ICD system 10 includes an ICD 14 connected to an extra-cardiovascular electrical stimulation and sensing lead 16. FIGS. 1A and 1B are described in the context of an ICD system 10 capable of providing defibrillation and/or cardioversion shocks and pacing pulses.

ICD 14 includes a housing 15 that forms a hermetic seal that protects internal components of ICD 14. The housing 15 of ICD 14 may be formed of a conductive material, such as titanium or titanium alloy. The housing 15 may function as a housing electrode (sometimes referred to as a can electrode). In examples described herein, housing 15 may be used as an active can electrode for use in delivering cardioversion/defibrillation (CV/DF) shocks or other high voltage pulses delivered using a high voltage therapy circuit. In other examples, housing 15 may be available for use in delivering unipolar, low voltage cardiac pacing pulses in conjunction with lead-based cathode electrodes. In other instances, the housing 15 of ICD 14 may include a plurality of electrodes on an outer portion of the housing. The outer portion(s) of the housing 15 functioning as an electrode(s) may be coated with a material, such as titanium nitride for reducing polarization artifact.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, sensors, electrical cardiac signal sensing circuitry, therapy delivery circuitry, power sources and other components for sensing cardiac electrical signals, detecting a heart rhythm, and controlling and delivering electrical stimulation pulses to treat an abnormal heart rhythm.

Lead 16 includes an elongated lead body 18 having a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead body 18 includes defibrillation electrodes 24 and 26 and pace/sense electrodes 28, 30 and 31. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently. In some instances, defibrillation electrodes 24 and 26 are coupled to electrically isolated conductors, and ICD 14 may include switching mechanisms to allow electrodes 24 and 26 to be utilized as a single defibrillation electrode (e.g., activated concurrently to form a common cathode or anode) or as separate defibrillation electrodes, (e.g., activated individually, one as a cathode and one as an anode or activated one at a time, one as an anode or cathode and the other remaining inactive with housing 15 as an active electrode).

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to low voltage pacing and sensing electrodes 28, 30 and 31. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage CV/DF shock therapy applications. Electrodes 24 and 26 may be used in a pacing electrode vector for delivering extra-cardiovascular pacing pulses such as anti-tachycardia pacing (ATP) pulses or bradycardia pacing pulses and/or in a sensing vector used to sense cardiac electrical signals and detect ventricular tachycardia (VT) and ventricular fibrillation (VF).

Electrodes 28, 30 and 31 are relatively smaller surface area electrodes for delivering low voltage pacing pulses and for sensing cardiac electrical signals. Electrodes 28, 30 and 31 are referred to as pace/sense electrodes because they are generally configured for use in relatively lower voltage applications than defibrillation electrodes 24 and 26, e.g., used as either a cathode or anode for delivery of pacing pulses and/or sensing of cardiac electrical signals. In some instances, electrodes 28, 30 and 31 may provide only pacing functionality, only sensing functionality or both.

In the example illustrated in FIGS. 1A and 1B, electrode 28 is located proximal to defibrillation electrode 24, and electrode 30 is located between defibrillation electrodes 24 and 26. A third pace/sense electrode 31 may be located distal to defibrillation electrode 26. Electrodes 28 and 30 are illustrated as ring electrodes, and electrode 31 is illustrated as a hemispherical tip electrode in the example of FIGS. 1A and 1B. However, electrodes 28, 30 and 31 may comprise any of a number of different types of electrodes, including ring electrodes, short coil electrodes, hemispherical electrodes, directional electrodes, segmented electrodes, or the like, and may be positioned at any position along lead body 18. Further, electrodes 28, 30 and 31 may be of similar type, shape, size and material or may differ from each other.

Lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum, substantially parallel to sternum 22. Although illustrated in FIGS. 1A and 1B as being offset laterally from and extending substantially parallel to sternum 22, lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of lead 16 may depend on the location of ICD 14, the arrangement and position of electrodes along lead body 18, and/or other factors.

Electrical conductors (not illustrated) extend through one or more lumens of the elongated lead body 18 of lead 16 from the lead connector at the proximal lead end 27 to electrodes 24, 26, 28, 30 and 31 located along the distal portion 25 of the lead body 18. Lead body 18 may be tubular or cylindrical in shape. In other examples, the distal portion 25 (or all of) the elongated lead body 18 may have a flat, ribbon or paddle shape. The lead body 18 may be formed from a non-conductive material, including silicone, polyurethane, fluoropolymers, mixtures thereof, and other appropriate materials, and shaped to form one or more lumens within which the one or more conductors extend. However, the techniques disclosed herein are not limited to such constructions or to any particular lead body design.

The elongated electrical conductors contained within the lead body 18 are each electrically coupled with respective defibrillation electrodes 24 and 26 and pace/sense electrodes 28, 30 and 31. Each of pacing and sensing electrodes 28, 30 and 31 are coupled to respective electrical conductors, which may be separate respective conductors within the lead body. The respective conductors electrically couple the electrodes 24, 26, 28, 30 and 31 to circuitry, such as a therapy circuit and/or a sensing circuit, of ICD 14 via connections in the connector assembly 17, including associated electrical feedthroughs crossing housing 15. The electrical conductors transmit therapy from a therapy circuit within ICD 14 to one or more of defibrillation electrodes 24 and 26 and/or pace/sense electrodes 28, 30 and 31 and transmit cardiac electrical signals from one or more of defibrillation electrodes 24 and 26 and/or pace/sense electrodes 28, 30 and 31 to the sensing circuit within ICD 14.

ICD 14 may obtain cardiac electrical signals corresponding to electrical activity of heart 8 via a combination of sensing vectors that include combinations of electrodes 28, 30, and/or 31. In some examples, housing 15 of ICD 14 is used in combination with one or more of electrodes 28, 30 and/or 31 in a sensing electrode vector. ICD 14 may even obtain cardiac electrical signals using a sensing vector that includes one or both defibrillation electrodes 24 and/or 26, e.g., between electrodes 24 and 26 or one of electrodes 24 or 26 in combination with one or more of electrodes 28, 30, 31, and/or housing 15.

ICD 14 analyzes the cardiac electrical signals received from one or more of the sensing vectors to monitor for abnormal rhythms, such as bradycardia, ventricular tachycardia (VT) or ventricular fibrillation (VF). ICD 14 may analyze the heart rate and/or morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated by reference herein in its entirety.

ICD 14 generates and delivers electrical stimulation therapy in response to detecting a tachyarrhythmia (e.g., VT or VF). ICD 14 may deliver ATP in response to VT detection, and in some cases may deliver ATP prior to a CV/DF shock or during high voltage capacitor charging in an attempt to avert the need for delivering a CV/DF shock. ATP may be delivered using an extra-cardiovascular pacing electrode vector selected from any of electrodes 24, 26, 28, 30, 31 and/or housing 15. The pacing electrode vector may be different than the sensing electrode vector. In one example, cardiac electrical signals are sensed between pace/sense electrodes 28 and 30, and ATP pulses (or other cardiac pacing pulses) are delivered between pace/sense electrode 30 used as a cathode electrode and defibrillation electrode 24 used as a return anode electrode. In other examples, cardiac pacing pulses may be delivered between pace/sense electrode 28 and either (or both) defibrillation electrode 24 or 26 or between defibrillation electrode 24 and defibrillation electrode 26. These examples are not intended to be limiting, and it is recognized that other sensing electrode vectors and cardiac pacing electrode vectors may be selected according to individual patient need.

If ATP does not successfully terminate VT or when VF is detected, ICD 14 may deliver one or more CV/DF shocks via one or both of defibrillation electrodes 24 and 26 and/or housing 15. ICD 14 may generate and deliver other types of electrical stimulation pulses such as post-shock pacing pulses or bradycardia pacing pulses using a pacing electrode vector that includes one or more of the electrodes 24, 26, 28, 30 and 31 and the housing 15 of ICD 14. As disclosed herein, ICD 14 may detect a need for an electrical stimulation therapy based on at least a rate of cardiac events sensed from a cardiac electrical signal received via one or more sensing electrode vector selected from the available electrodes 24, 26, 28, 30 and 31 and housing 15. A fast rate of sensed cardiac events may lead to determining a need for ATP and/or a CV/DF shock. A slow rate of cardiac events may lead to cardiac pacing according to a programmed pacing protocol or mode, e.g., VVI pacing or post-shock pacing. For example, ICD 14 may detect a need for a pacing therapy based on a pacing interval expiring before a cardiac event is sensed, indicating a slow rate of cardiac events below a programmed lower pacing rate.

FIGS. 1A and 1B are illustrative in nature and should not be considered limiting of the practice of the techniques disclosed herein. In other examples, lead 16 may include less than three pace/sense electrodes or more than three pace/sense electrodes and/or a single defibrillation electrode or more than two electrically isolated or electrically coupled defibrillation electrodes or electrode segments. The pace/sense electrodes 28, 30 and/or 31 may be located elsewhere along the length of lead 16. For example, lead 16 may include a single pace/sense electrode 30 between defibrillation electrodes 24 and 26 and no pace/sense electrode distal to defibrillation electrode 26 or proximal defibrillation electrode 24. Various example configurations of extra-cardiovascular leads and electrodes and dimensions that may be implemented in conjunction with the extra-cardiovascular pacing techniques disclosed herein are described in commonly-assigned, pending U.S. Publication No. 2015/0306375 (Marshall, et al.) and U.S. Publication No. 2015/0306410 (Marshall, et al.), both of which are incorporated herein by reference in their entirety.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferior from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space.

An external device 40 is shown in telemetric communication with ICD 14 by a communication link 42. External device 40 may include a processor 52, memory 53, display 54, user interface 56 and telemetry unit 58. Processor 52 controls external device operations and processes data and signals received from ICD 14. Display 54, which may include a graphical user interface, displays data and other information to a user for reviewing ICD operation and programmed parameters as well as cardiac electrical signals retrieved from ICD 14. For example, as described in conjunction with FIGS. 10 and 11, a clinician may view cardiac electrical signals received from ICD 14 during VF induction for testing programmed sensitivity settings and during normal sinus rhythm for reviewing and selecting programmable R-wave sensing threshold parameter settings.

User interface 56 may include a mouse, touch screen, key pad or the like to enable a user to interact with external device 40 to initiate a telemetry session with ICD 14 for retrieving data from and/or transmitting data to ICD 14, including programmable parameters for controlling a cardiac event sensing threshold as described herein. Telemetry unit 58 includes a transceiver and antenna configured for bidirectional communication with a telemetry circuit included in ICD 14 and is configured to operate in conjunction with processor 52 for sending and receiving data relating to ICD functions via communication link 42.

Communication link 42 may be established between ICD 14 and external device 40 using a radio frequency (RF) link such as BLUETOOTH®, Wi-Fi, or Medical Implant Communication Service (MICS) or other RF or communication frequency bandwidth or communication protocols. Data stored or acquired by ICD 14, including physiological signals or associated data derived therefrom, results of device diagnostics, and histories of detected rhythm episodes and delivered therapies, may be retrieved from ICD 14 by external device 40 following an interrogation command.

External device 40 may be embodied as a programmer used in a hospital, clinic or physician's office to retrieve data from ICD 14 and to program operating parameters and algorithms in ICD 14 for controlling ICD functions. External device 40 may alternatively be embodied as a home monitor or hand held device. External device 40 may be used to program cardiac signal sensing parameters, cardiac rhythm detection parameters and therapy control parameters used by ICD 14. At least some control parameters used to control a cardiac event sensing threshold, e.g., the R-wave sensing threshold, according to techniques disclosed herein may be programmed into ICD 14 using external device 40.

Figure 2A:
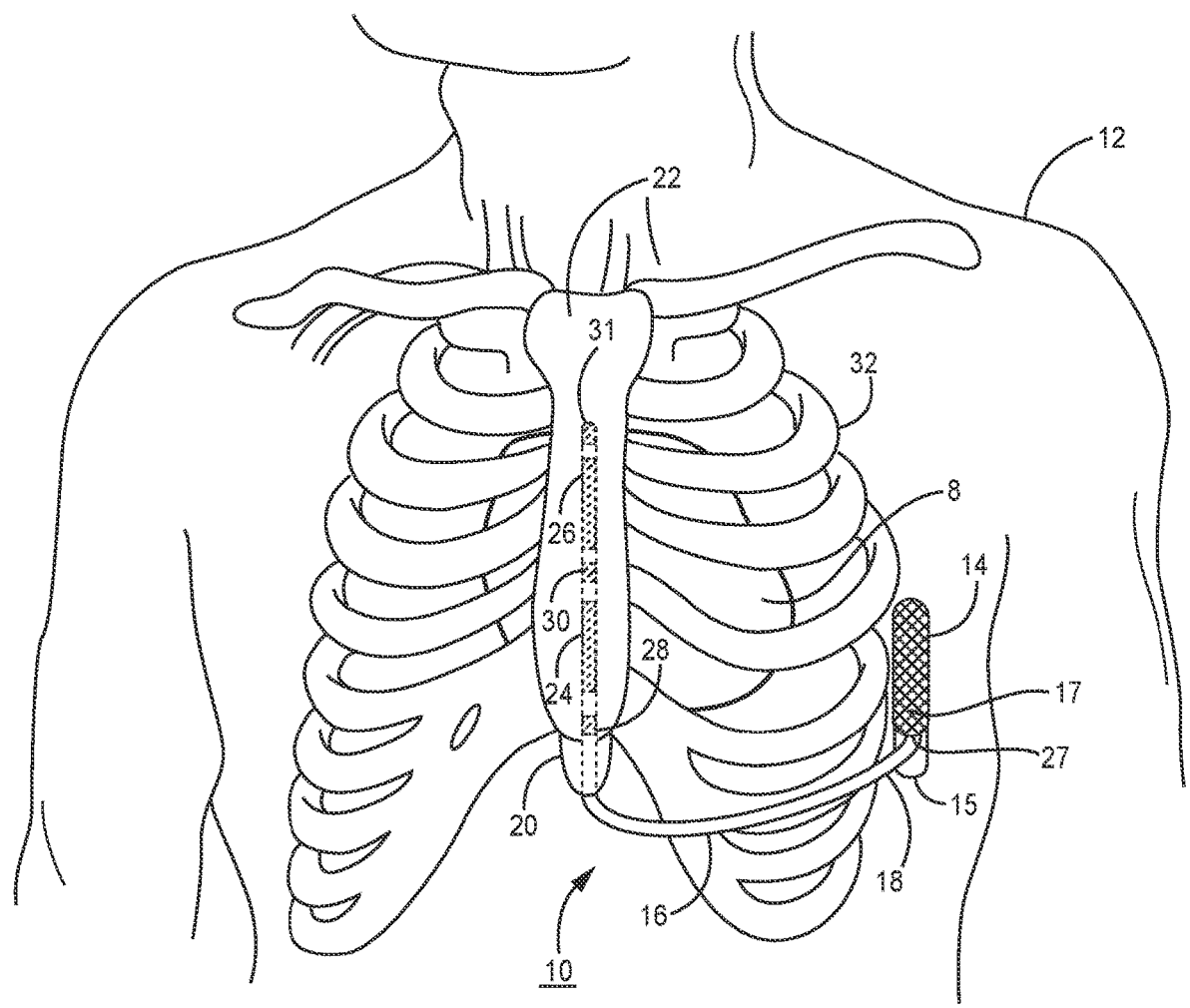
FIGS. 2A-2C are conceptual diagrams of a patient implanted with the extra-cardiovascular ICD system of FIG. 1A in a different implant configuration.
Figure 2B:
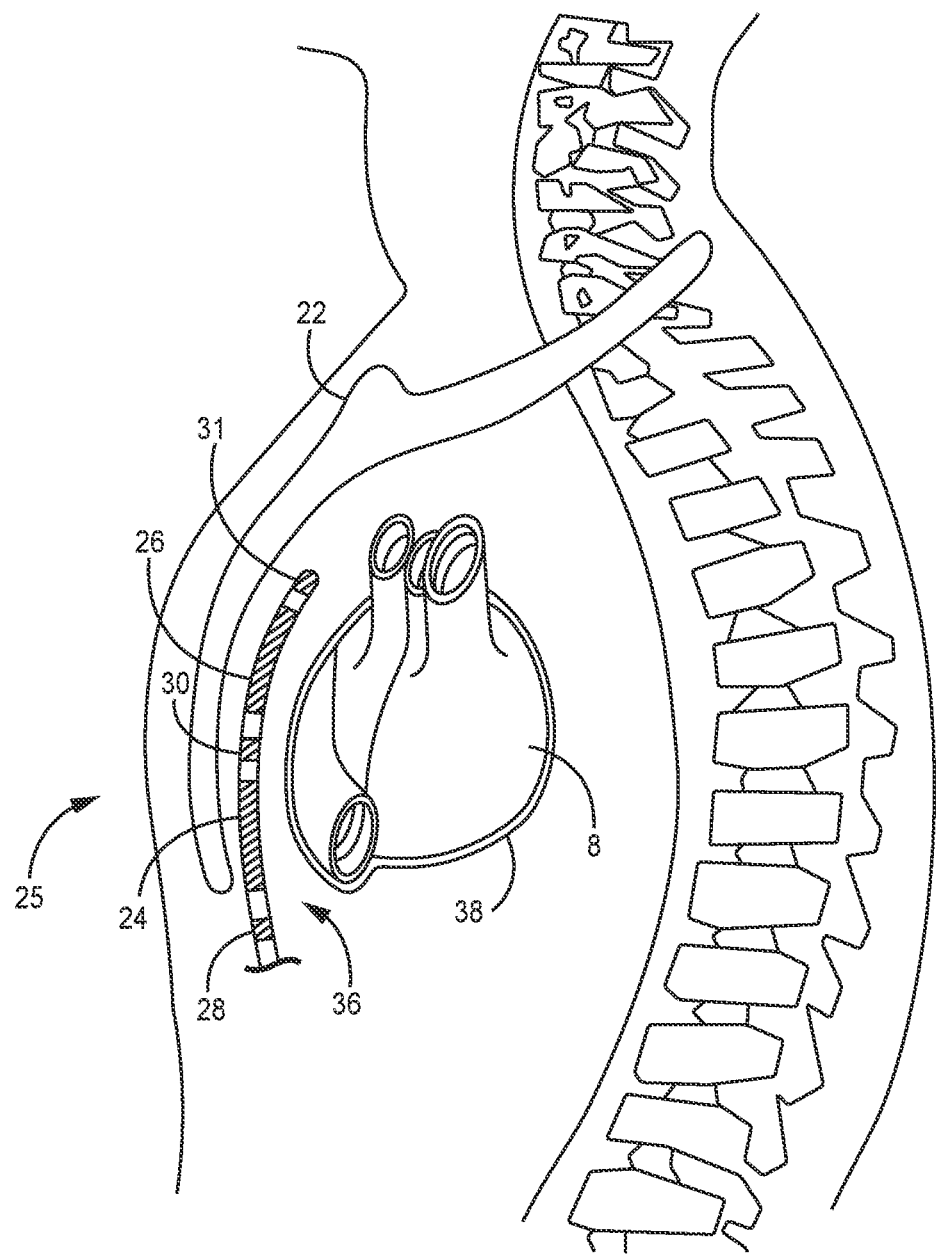
Figure 2C:
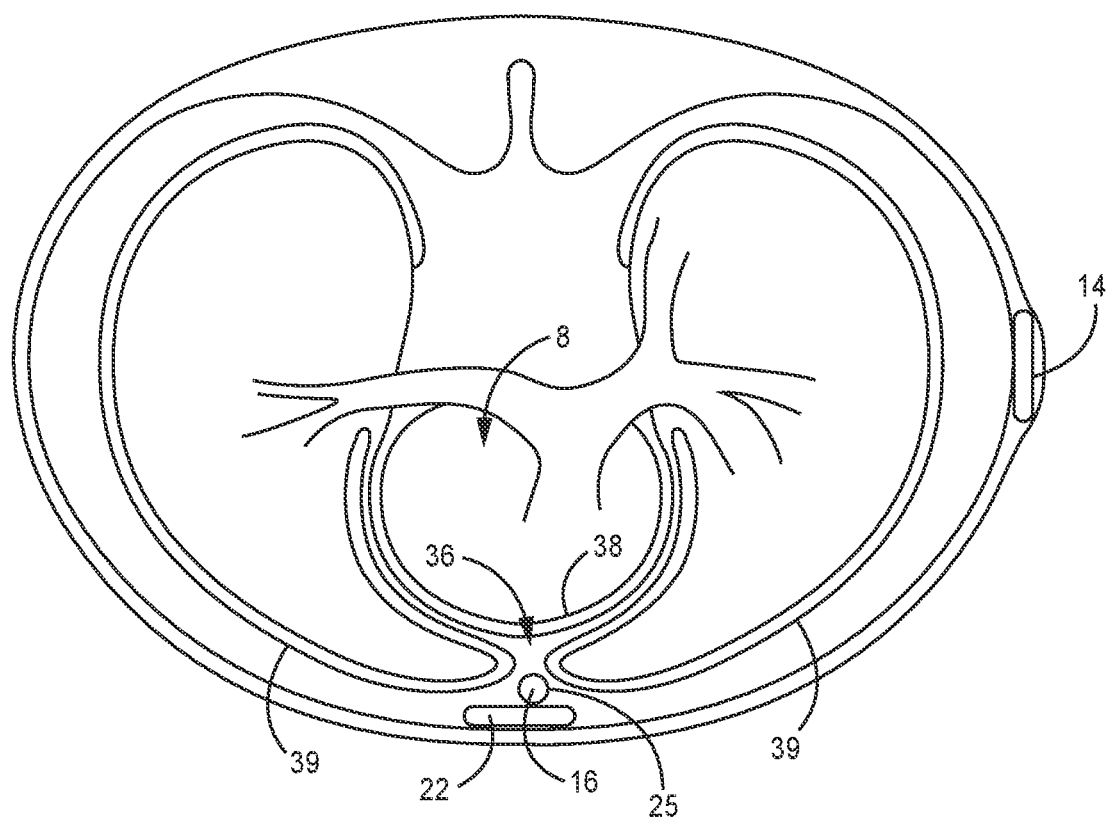

FIGS. 2A-2C are conceptual diagrams of patient 12 implanted with extra-cardiovascular ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22. In some instances, the anterior wall of anterior mediastinum 36 may also be formed by the transversus thoracis muscle and one or more costal cartilages. Anterior mediastinum 36 includes a quantity of loose connective tissue (such as areolar tissue), adipose tissue, some lymph vessels, lymph glands, substernal musculature, small side branches of the internal thoracic artery or vein, and the thymus gland. In one example, the distal portion 25 of lead 16 extends along the posterior side of sternum 22 substantially within the loose connective tissue and/or substernal musculature of anterior mediastinum 36.

A lead implanted such that the distal portion 25 is substantially within anterior mediastinum 36 may be referred to as a "substernal lead." In the example illustrated in FIGS. 2A-2C, the distal portion 25 of lead body 18 is located substantially centered under sternum 22. In other instances, however, the distal portion 25 may be implanted such that it is offset laterally from the center of sternum 22. In some instances, lead 16 may extend laterally such that distal portion 25 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of or adjacent to the pericardium 38 of heart 8. Other implant locations and lead and electrode arrangements that may be used in conjunction with the techniques described herein are generally disclosed in the incorporated patent references.

Figure 3:
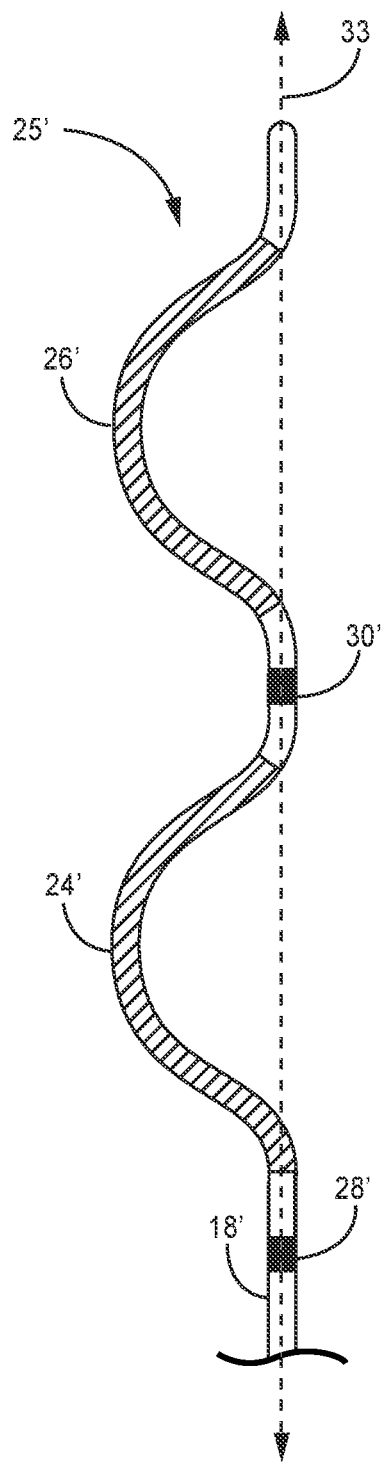
FIG. 3 is a conceptual diagram of a distal portion of an extra-cardiovascular lead having an electrode configuration according to another example.

FIG. 3 is a conceptual diagram illustrating a distal portion 25' of another example of extra-cardiovascular lead 16 of FIGS. 1A-2C having a curving distal portion 25' of lead body 18'. Lead body 18' may be formed having an undulating, curving, bending, serpentine, or zig-zagging shape along distal portion 25'. In the example shown, defibrillation electrodes 24' and 26' are carried along pre-formed curving portions of the lead body 18'. Pace/sense electrode 30' is carried in between defibrillation electrodes 24' and 26'. Pace/sense electrode 28' is carried proximal to the proximal defibrillation electrode 24'. No electrode is provided distal to defibrillation electrode 26' in this example.

As shown in FIG. 3, lead body 18' may be formed having a curving distal portion 25' that includes two "C" shaped curves, which together may resemble the Greek letter epsilon, "ε." Defibrillation electrodes 24' and 26' are each carried by one of the two respective C-shaped portions of the lead body distal portion 25', which extend or curve in the same direction away from a central axis 33 of lead body 18'. In the example shown, pace/sense electrode 28' is proximal to the C-shaped portion carrying electrode 24', and pace/sense electrode 30' is proximal to the C-shaped portion carrying electrode 26'. Pace/sense electrodes 28' and 30' may, in some instances, be approximately aligned with the central axis 33 of the straight, proximal portion of lead body 18' such that mid-points of defibrillation electrodes 24' and 26' are laterally offset from electrodes 28' and 30'. Other examples of extra-cardiovascular leads including one or more defibrillation electrodes and one or more pacing and sensing electrodes carried by curving, serpentine, undulating or zig-zagging distal portion of the lead body that may be implemented with the pacing techniques described herein are generally disclosed in pending U.S. Pat. Publication No. 2016/0158567 (Marshall et al.), incorporated herein by reference in its entirety.

Figure 4:
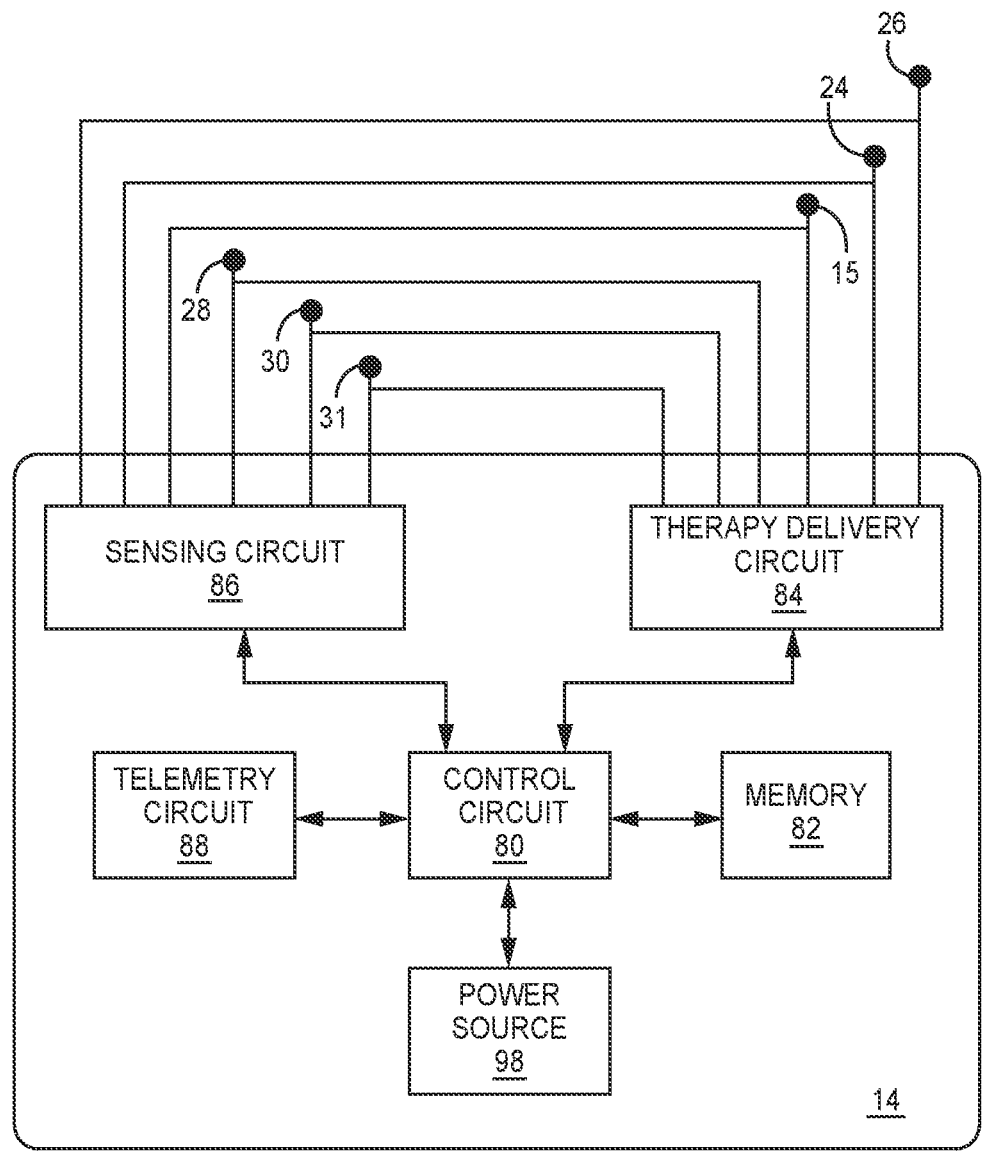
FIG. 4 is a schematic diagram of the ICD of FIGS. 1A-2C according to one example.

FIG. 4 is a schematic diagram of ICD 14 according to one example. The electronic circuitry enclosed within housing 15 (shown schematically as an electrode in FIG. 4) includes software, firmware and hardware that cooperatively monitor one or more cardiac electrical signals, determine when an electrical stimulation therapy is necessary, and deliver therapy as needed according to programmed therapy delivery algorithms and control parameters. The software, firmware and hardware are configured to detect and discriminate VT and VF for determining when ATP or CV/DF shocks are required and may determine when bradycardia pacing, post-shock pacing, rate-responsive pacing or other types of electrical stimulation is needed. ICD 14 is coupled to an extra-cardiovascular lead, such as lead 16 carrying extra-cardiovascular electrodes 24, 26, 28, 30, and 31, as shown in FIG. 1A, for delivering electrical stimulation pulses to the patient's heart and for sensing cardiac electrical signals.

ICD 14 includes a control circuit 80, memory 82, therapy delivery circuit 84, sensing circuit 86, and telemetry circuit 88. A power source 98 provides power to the circuitry of ICD 14, including each of the circuits 80, 82, 84, 86, and 88 as needed. Power source 98 may include one or more energy storage devices, such as one or more rechargeable or non-rechargeable batteries. The connections between power source 98 and each of the other circuits 80, 82, 84, 86 and 88 are to be understood from the general block diagram of FIG. 4, but are not shown for the sake of clarity. For example, power source 98 may be coupled to a low voltage (LV) charging circuit and to a high voltage (HV) charging circuit included in therapy delivery circuit 84 for charging low voltage and high voltage capacitors, respectively, included in therapy delivery circuit 84 for producing respective low voltage pacing pulses, such as bradycardia pacing, post-shock pacing or ATP pulses, or for producing relatively higher voltage pulses, such as CV/DF shock pulses or higher voltage pacing pulses. In some examples, high voltage capacitors are charged and utilized for delivering pacing pulses instead of low voltage capacitors.

The circuits shown in FIG. 4 represent functionality included in ICD 14 and may include any discrete and/or integrated electronic circuit components that implement analog and/or digital circuits capable of producing the functions attributed to ICD 14 herein. The various circuits may include one or more of an application specific integrated circuit (ASIC), an electronic circuit, a processor (shared, dedicated, or group) and memory that execute one or more software or firmware programs, a combinational logic circuit, state machine, or other suitable components or combination of components that provide the described functionality. The particular form of software, hardware and/or firmware employed to implement the functionality disclosed herein will be determined primarily by the particular system architecture employed in the ICD and by the particular detection and therapy delivery methodologies employed by the ICD. Providing software, hardware, and/or firmware to accomplish the described functionality in the context of any modern IMD system, given the disclosure herein, is within the abilities of one of skill in the art.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 and/or other ICD circuits to perform various functions attributed to ICD 14 or those ICD circuits. The non-transitory computer-readable media storing the instructions may include any of the media listed above.

The functions attributed to ICD 14 herein may be embodied as one or more integrated circuits. Depiction of different circuits is intended to highlight different functional aspects and does not necessarily imply that such circuits must be realized by separate hardware or software components. Rather, functionality associated with one or more circuits may be performed by separate hardware, firmware or software components, or integrated within common hardware, firmware or software components. For example, sensing operations may be performed by sensing circuit 86 under the control of control circuit 80 and may include operations implemented in a processor executing instructions stored in memory 82 and control signals such as timing and sensing threshold amplitude signals sent from control circuit 80 to sensing circuit 86.

Control circuit 80 communicates, e.g., via a data bus, with therapy delivery circuit 84 and sensing circuit 86 for sensing cardiac electrical activity, detecting cardiac rhythms, and controlling delivery of cardiac electrical stimulation therapies in response to sensed cardiac signals. Therapy delivery circuit 84 and sensing circuit 86 are electrically coupled to electrodes 24, 26, 28, 30 and 31 (if present) carried by lead 16 and the housing 15, which may function as a common or ground electrode or as an active can electrode for delivering CV/DF shock pulses or cardiac pacing pulses.

Sensing circuit 86 may be selectively coupled to electrodes 28, 30 and 31 and/or housing 15 in order to monitor electrical activity of the patient's heart. Sensing circuit 86 may additionally be selectively coupled to defibrillation electrodes 24 and/or 26 for use in a sensing electrode vector. Sensing circuit 86 is enabled to selectively monitor one or more sensing vectors at a time selected from the available electrodes 24, 26, 28, 30, 31 and housing 15. For example, sensing circuit 86 may include switching circuitry for selecting which of electrodes 24, 26, 28, 30, 31 and housing 15 are coupled to sense amplifiers or other cardiac event detection circuitry included in sensing circuit 86. Switching circuitry may include a switch array, switch matrix, multiplexer, or any other type of switching device suitable to selectively couple components of sensing circuit 86 to selected electrodes. In some instances, control circuit 80 may control the switching circuitry to selectively couple sensing circuit 86 to one or more sense electrode vectors. The cardiac event detection circuitry within sensing circuit 86 may include one or more sense amplifiers, filters, rectifiers, threshold detectors, comparators, analog-to-digital converters (ADCs), or other analog or digital components.

In some examples, sensing circuit 86 includes multiple sensing channels for acquiring cardiac electrical signals from multiple sensing vectors selected from electrodes 24, 26, 28, 30, 31 and housing 15. Each sensing channel may be configured to amplify, filter and rectify the cardiac electrical signal received from selected electrodes coupled to the respective sensing channel to improve the signal quality for sensing cardiac events, such as R-waves. For example, each sensing channel may include a pre-filter and amplifier for filtering and amplifying a signal received from a selected pair of electrodes. The resulting raw cardiac electrical signal may be passed from the pre-filter and amplifier to a post-filter and amplifier, analog-to-digital converter, rectifier, and cardiac event detector that compares the digitized, filtered and rectified cardiac electrical signal to a cardiac event sensing threshold for sensing cardiac events from the received cardiac electrical signal. The cardiac event detector may include a sense amplifier, comparator or other detection circuitry that senses a cardiac event when the cardiac electrical signal crosses the cardiac event sensing threshold. The cardiac event sensing threshold is automatically adjusted by sensing circuit 86 under the control of control circuit 80, based on timing intervals and sensing threshold values determined by control circuit 80, stored in memory 82, and/or controlled by hardware of control circuit 80 and/or sensing circuit 86. Some sensing threshold control parameters may be programmed by a user and passed from control circuit 80 to sensing circuit 86 via a data bus.

As described herein, sensing circuit 86 may sense R-waves according to a sensing threshold that is automatically adjusted to multiple threshold levels at specified times after a sensing threshold crossing or after an electrical stimulation pulse delivered by therapy delivery circuit 84. Multiple threshold levels and the time intervals over which each threshold level or value is applied may be used to provide accurate R-wave sensing while minimizing T-wave oversensing and P-wave oversensing. If T-waves and/or P-waves are falsely sensed as R-waves, due to a cardiac electrical signal crossing the R-wave sensing threshold, a tachyarrhythmia may be falsely detected potentially leading to an unnecessary cardiac electrical stimulation therapy, such as ATP or shock delivery. This situation is avoided using the multi-level sensing threshold techniques disclosed herein while still providing VT and VF detection with a high sensitivity. Oversensing may also cause ICD 14 to inhibit bradycardia pacing pulses when pacing is actually needed. By avoiding oversensing using the multi-level sensing threshold, inhibiting of bradycardia pacing pulses when pacing is actually needed is avoided.

Upon sensing a cardiac event based on a sensing threshold crossing, sensing circuit 86 may produce a sensed event signal, such as an R-wave sensed event signal, that is passed to control circuit 80. The sensed event signals are used by control circuit 80 for detecting cardiac rhythms and determining a need for therapy. For example, time intervals between consecutive sensed event signals may be determined and compared to tachyarrhythmia detection intervals for detecting a tachyarrhythmia and thereby determine a need for an electrical stimulation therapy to treat the detected tachyarrhythmia. Sensing circuit 86 may also pass a digitized electrocardiogram (ECG) signal to control circuit 80 for morphology analysis performed for detecting and discriminating heart rhythms. In some examples, analysis of the digitized cardiac electrical signal is performed for determining R-wave sensing threshold control parameters as described in conjunction with FIG. 11.

Signals from the selected sensing vector may be passed through a bandpass filter and amplifier, provided to a multiplexer and thereafter converted to multi-bit digital signals by an analog-to-digital converter, all included in sensing circuit 86, for storage in random access memory included in memory 82 under control of a direct memory access circuit via a data/address bus. Control circuit 80 may be a microprocessor based controller that employs digital signal analysis techniques to characterize the digitized signals stored in random access memory of memory 82 to recognize and classify the patient's heart rhythm employing any of numerous signal processing methodologies for analyzing cardiac signals and cardiac event waveforms, e.g., R-waves. Examples of algorithms that may be performed by ICD 14 for detecting, discriminating and treating tachyarrhythmia which may be adapted to utilize techniques disclosed herein for controlling a multi-level cardiac event sensing threshold for sensing cardiac electrical signals are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety.

Therapy delivery circuit 84 includes charging circuitry, one or more charge storage devices, such as one or more high voltage capacitors and in some examples one or more low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80. Control circuit 80 may include various timers or counters that control when ATP or other cardiac pacing pulses are delivered.

For example, control circuit 80 may include pacer timing and control circuitry having programmable digital counters set by the microprocessor of the control circuit 80 for controlling the basic time intervals associated with various pacing modes or anti-tachycardia pacing sequences delivered by ICD 14. The microprocessor of control circuit 80 may also set the amplitude, pulse width, polarity or other characteristics of the cardiac pacing pulses, which may be based on programmed values stored in memory 82.

During pacing, escape interval counters within the pacer timing and control circuitry are reset upon sensing of an intrinsic R-wave as indicated by an R-wave sensed event signal from sensing circuit 86 and upon generation of a pacing pulse. In accordance with the selected mode of pacing, pacing pulses are generated by a pulse output circuit of therapy delivery circuit 84 if an escape interval expires without being reset due to an R-wave sensed event signal. The pace output circuit is coupled to the desired electrodes via switch matrix for discharging one or more capacitors across the pacing load. The durations of the escape intervals are determined by control circuit 80 via a data/address bus. The value of the count present in the escape interval counters when reset by sensed R-waves can be used to measure R-R intervals for detecting the occurrence of a variety of arrhythmias. As described in conjunction with the diagrams and flow charts that follow, sensing circuit 86 may be configured to control the R-wave sensing threshold used for sensing R-waves from a received cardiac electrical signal according to post-sense control parameters and according to post-pulse control parameters. One or more time intervals and/or sensing threshold values used to control the R-wave sensing threshold following an electrical stimulation pulse, e.g., a pacing pulse or CV/DF shock pulse, may be different than the time intervals and/or sensing threshold values used to control the R-wave sensing threshold following a sensed intrinsic R-wave.

Memory 82 includes read-only memory (ROM) in which stored programs controlling the operation of the control circuit 80 reside. Memory 82 may further include random access memory (RAM) configured as a number of recirculating buffers capable of holding a series of measured intervals, counts or other data for analysis by the control circuit 80 for predicting or diagnosing an arrhythmia.

In response to the detection of VT, ATP therapy can be delivered by loading a regimen from the microprocessor included in control circuit 80 into the pacer timing and control circuit according to the type and rate of tachycardia detected. In the event that higher voltage cardioversion or defibrillation pulses are required, the control circuit microprocessor activates cardioversion and defibrillation control circuitry included in control circuit 80 to initiate charging of the high voltage capacitors of via a charging circuit, both included in therapy delivery circuit 84, under the control of a high voltage charging control line. The voltage on the high voltage capacitors is monitored via a voltage capacitor line, which is passed to control circuit 80. When the voltage reaches a predetermined value set by the microprocessor of control circuit 80, a logic signal is generated on a capacitor full line passed to therapy delivery circuit 84, terminating charging. The CV/DF pulse is delivered to the heart by an output circuit of therapy delivery circuit 84 under the control of the pacer timing and control circuitry via a control bus. The output circuit determines the electrodes used for delivering the CV/DF pulse and the pulse wave shape. Therapy delivery and control circuitry generally disclosed in any of the above-incorporated patents may be implemented in ICD 14.

Control parameters utilized by control circuit 80 for detecting cardiac rhythms and controlling therapy delivery may be programmed into memory 82 via telemetry circuit 88. Telemetry circuit 88 includes a transceiver and antenna for communicating with external device 40 (shown in FIG. 1A), e.g., using RF communication as described above. Under the control of control circuit 80, telemetry circuit 88 may receive downlink telemetry from and send uplink telemetry to external device 40. In some cases, telemetry circuit 88 may be used to transmit and receive communication signals to/from another medical device implanted in patient 12.

Figure 5:
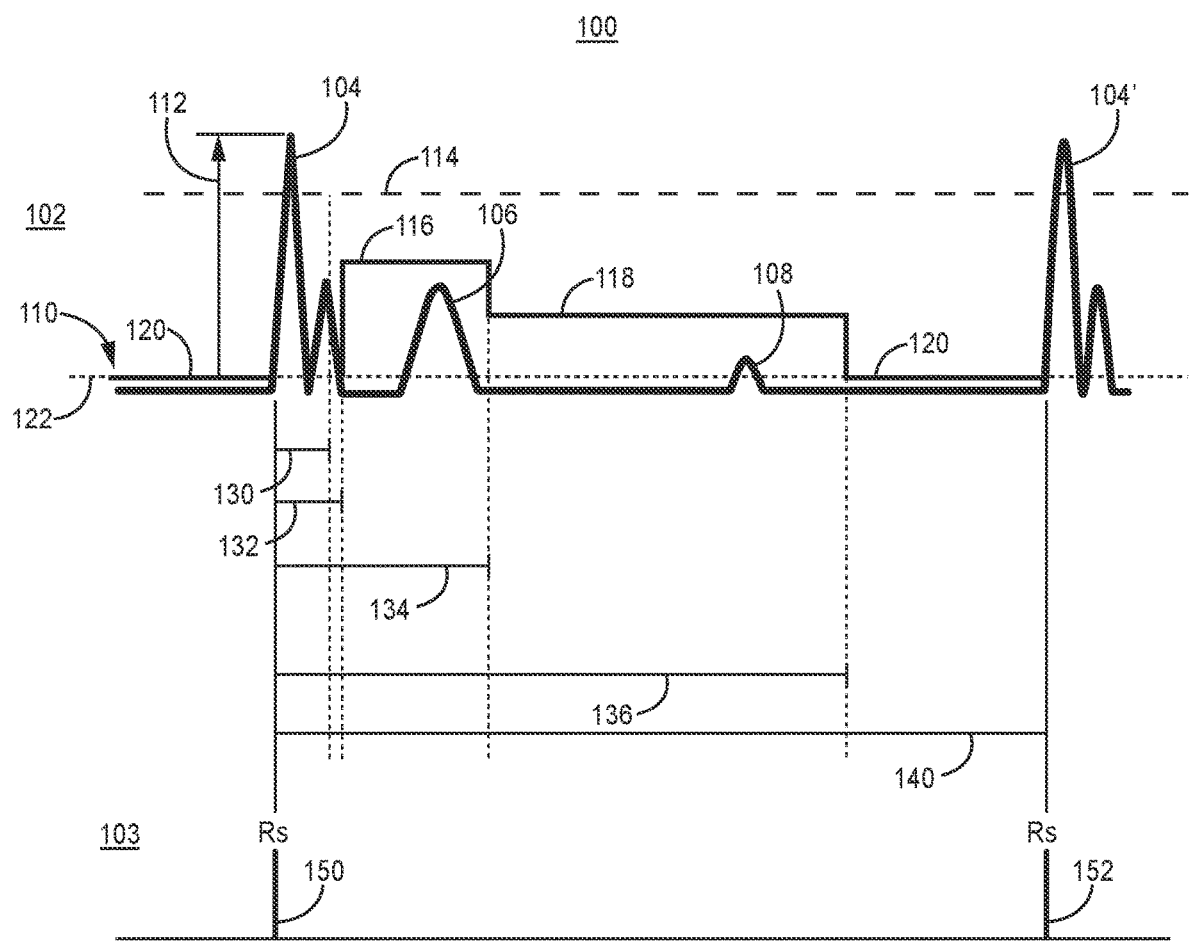
FIG. 5 is a timing diagram showing a filtered and rectified cardiac electrical signal and R-wave sensed event signals produced by a sensing circuit of the ICD of FIG. 4.

FIG. 5 is a timing diagram 100 showing a band-pass filtered and rectified cardiac electrical signal 102 and R-wave sensed event signals 103 produced by sensing circuit 86. The cardiac electrical signal 102 includes R-waves 104, 104', T-wave 106, and P-wave 108. As used herein, "R-wave sensing" generally refers to sensing the intrinsic QRS complex of a cardiac electrical signal for the purposes of detecting and discriminating intrinsic ventricular rhythms, e.g., for detecting and discriminating ventricular fibrillation, ventricular tachycardia, supraventricular tachycardia, bradycardia, asystole or other types of intrinsic heart rhythms. Sensing circuit 86 automatically adjusts an R-wave sensing threshold 110 to multiple threshold values 116, 118, and 120. The multiple threshold values 116, 118, and 120 may be determined by control circuit 80 based on the maximum peak amplitude 112 of a sensed R-wave 104 and passed to sensing circuit 86 along with multiple timing intervals 130, 132, 134 and 136 for controlling the R-wave sensing threshold 110 for detecting of the next R-wave 104'. Threshold values 116, 118 and 120 of R-wave sensing threshold 110 may also be referred to as threshold "levels" or "settings" or merely as "thresholds" but all refer to different voltage amplitudes which, when crossed by a positive-going, rectified band-pass filtered cardiac electrical signal, result in an R-wave sensed event signal being produced by sensing circuit 86.

In the example shown, R-wave 104 is sensed by sensing circuit 86 when the cardiac electrical signal 102 crosses R-wave sensing threshold 110, which is set to threshold value 120 at the time of the threshold crossing. An R-wave sensed event signal 150 is generated. Upon sensing the R-wave 104, a post-sense blanking interval 130 may be started. The post-sense blanking interval may be a fixed time interval controlled by hardware that prevents the R-wave 104 from being sensed twice. The post-sense blanking interval 130 is 120 ms in one example, and may be 120 ms to 160 ms in other examples. During the post-sense blanking interval 130, a peak detector circuit included in sensing circuit 86 or control circuit 80 determines the maximum peak amplitude 112 of R-wave 104.

At the expiration of the post-sense blanking interval 130, the maximum peak amplitude 112 is used to determine the sensing threshold values 116 and 118. In one example, a second blanking interval 132 is started upon sensing R-wave 104 and is slightly longer than the first blanking interval 130. Upon expiration of the first blanking interval 130, a microprocessor within control circuit 80 may fetch the R-wave peak amplitude and determine the first, starting threshold value 116 prior to expiration of the second blanking interval 132. The R-wave sensing threshold 110 may be set to the starting threshold value 116 upon expiration of the second blanking interval 132.

The second blanking interval 132 may be at least 20 ms longer than the first blanking interval 130. For example, second blanking interval 132 may be 140 ms to 180 ms long in some examples. In some implementations, the first blanking interval 130 is a hardware controlled blanking interval, and the second blanking interval 132 is a digital blanking interval controlled by firmware or software stored in memory 82. The second blanking interval 132 may be a user-programmable value so that it may be tailored to the patient, e.g., based on the width of R-wave 104.

The control circuit 80 may determine the first, starting threshold value 116 as a percentage of the R-wave peak amplitude 112 during the interval between the expiration of the first blanking interval 130 and the expiration of the second blanking interval 132. This interval difference between the first and second blanking intervals 130 and 132 may be minimized in some examples to enable firmware processing time to determine the first, starting threshold value 116 but enable R-wave sensing as early as possible after expiration of the first blanking interval 130.

By implementing the second blanking interval 132 and computation of the starting threshold value 116 in firmware stored in memory 82 and executed by a microprocessor of control circuit 80, the multi-level R-wave sensing threshold 110 disclosed herein may be implemented in many existing IMD systems that already include a hardware-implemented blanking interval without requiring hardware modifications. The longer second blanking interval 132 may be fixed or programmable to account for wider R-waves that typically appear in a cardiac signal obtained using extra-cardiovascular electrodes compared to the R-wave width in intracardiac electrogram signals. Furthermore, implementation of the second blanking interval 132 as a digital blanking interval allows R-wave sensing threshold control techniques disclosed herein to operate in conjunction with other algorithms or methods being executed by hardware or firmware of ICD 14 for heart rhythm detection without modification. For example, ICD 14 may be configured to execute T-wave oversensing rejection algorithms implemented in hardware or firmware configured to determine a differential filtered cardiac electrical signal as generally disclosed in U.S. Pat. No. 7,831,304 (Cao, et al.), incorporated herein by reference in its entirety. By setting the second blanking interval 132 as a digital blanking interval controlled by firmware, the R-wave sensing threshold 110 may be controlled without altering operations performed by a T-wave oversensing rejection algorithm operating concurrently, which may be implemented in hardware.

In other examples, the first blanking interval 130, peak detector for determining R-wave peak amplitude 112, and the second blanking interval 132 may all be implemented in hardware, all be implemented in firmware or a combination of both. In some examples, the second blanking interval 132 may be programmable such that the time of the onset of R-wave sensing at the expiration of the second blanking interval 132, after the expiration of the first blanking interval 130, may be selected by a user according to patient need. When peak detection and determination of the starting threshold value 116 are implemented in hardware, a single hardware implemented blanking interval 130 may be used without requiring a second blanking interval 132 for providing firmware processing time during which the starting threshold value 116 is determined.

The first sensing threshold value 116 may set to a percentage of the R-wave peak amplitude 112. For example, the first sensing threshold value 116 may be 50% of peak amplitude 112, and may be from 40% to 60% in other examples. The percentage of R-wave peak amplitude 112 used to determine the starting threshold value 116 is selected to promote a high likelihood that the threshold value 116 is greater than the maximum amplitude of T-wave 106. The percentage of peak amplitude 112 used to determine starting threshold value 116 may be selected based on a previous baseline T-wave amplitude measurement or T/R amplitude ratio. The starting threshold value 116 is held constant over a sense delay interval 134 in the example shown to maintain the R-wave sensing threshold 110 above a maximum T-wave amplitude until a time point near the end or after the T-wave 106. In other examples, the R-wave sensing threshold 110 may have a starting threshold value 116 that slowly decays over the sense delay interval 134. The decay rate, however, is selected to be relatively slow so that the ending threshold value at the expiration of the sense delay interval 134 is still greater than an expected T-wave amplitude.

Sense delay interval 134 may be started upon sensing R-wave 104, as shown in FIG. 5. Alternatively, sense delay interval 134 may be started upon expiration of the second blanking interval 132. Sense delay interval 134 may be a user-programmable interval which may be tailored to patient need to encompass the T-wave 106, or at least the peak of the T-wave 106, or a majority of the T-wave 106, to avoid T-wave oversensing. Sense delay interval 134 is 360 ms in one example and may be, with no limitation intended, 300 ms to 400 ms in other examples. By allowing a user to program the sense delay interval 134, the user has the ability to make adjustments to how early after a sensed R-wave the sensing threshold 110 is adjusted to a lower value, e.g., threshold value 118. In this way, if T-wave oversensing is being detected or reported by the ICD 14 or is being observed in cardiac electrical signal episodes that are stored by ICD 14 and transmitted to external device 40, the clinician has the ability to increase the sense delay interval 134 to avoid future T-wave oversensing without compromising detection of ventricular fibrillation or ventricular tachycardia.

Control circuit 80 may be configured to detect T-wave oversensing when it occurs and reject RR-intervals or other evidence of VT or VF when T-wave oversensing is detected. Examples of T-wave oversensing rejection algorithms that may be included in ICD 14 are generally disclosed in the above-incorporated '304 patent (Cao, et al.) and in U.S. Pat. No. 8,886,296 (Patel, et al.) and U.S. Pat. No. 8,914,106 (Charlton, et al.), also incorporated herein by reference in their entirety. In some examples, control circuit 80 may automatically increase the sense delay interval 134 and/or increase the starting value 116 of R-wave sensing threshold 110 in response to T-wave oversensing detection. Sense delay interval 134 may be increased up to a predefined maximum limit, e.g., 440 ms. If there is no TWOS detected for a predetermined time interval, for example one minute, one hour or one day, or if a tachyarrhythmia episode is being detected (e.g., three or more VT or VF intervals detected), sense delay interval 134 may be automatically reduced to a shorter interval or to a previous setting by control circuit 80.

In some examples, sense delay interval 134 is set equal to the tachycardia detection interval (TDI) used by control circuit 80 for detecting ventricular tachycardia (VT). Alternatively, sense delay interval 134 may be set slightly longer than the TDI, e.g., 10 to 20 ms longer than the TDI. Intervals between consecutively sensed R-waves, for example RR interval 140 between two consecutive R-wave sensed event signals 150 and 152 shown in FIG. 5, are compared to the TDI and to a fibrillation detection interval (FDI) by a cardiac rhythm analyzer included in control circuit 80. If an RR interval is less than the TDI, the cardiac rhythm analyzer may increase a VT interval counter. If the RR interval is less than the FDI, the cardiac rhythm analyzer may increase a VF interval counter. If the VT counter reaches a number of intervals to detect (NID) VT, VT is detected. If the VF counter reaches an NID to detect VF, VF is detected. By setting sense delay interval 134 equal to a programmed TDI, the R-wave sensing threshold 110 is kept high, at the starting threshold value 116, throughout the FDI and the TDI (which is longer than the FDI) such that the likelihood of a falsely sensed R-wave due to T-wave oversensing during the TDI is minimized, minimizing the likelihood of an oversensed T-wave contributing to a VT or VF detection. If the T-wave 106 exceeds a lower value of R-wave sensing threshold 110 at an interval after the R-wave 104 that is longer than the TDI, the T-wave oversensed event will not contribute to VT detection. Accordingly, the sense delay interval 134 may be set to match the TDI programmed for VT detection and may be automatically adjusted to track the TDI if the TDI is reprogrammed to a different value.

Upon expiration of the sense delay interval 134, the sensing circuit 86 adjusts R-wave sensing threshold 110 to a second threshold value 118, lower than the starting value 116. The second threshold value 118 may be determined as a percentage of the R-wave peak amplitude 112. In one example, threshold value 118 is set to approximately 28% of the R-wave peak amplitude 112. Threshold value 118 may be set to 20% to 30% of the R-wave peak amplitude 112 in other examples. The second threshold value 118 is set to a value that is expected to be greater than the peak amplitude of the P-wave 108. P-waves are generally much lower in amplitude than R-waves, however, depending on the alignment of the sensing electrode vector relative to the cardiac axis and other factors, P-wave oversensing can occur in some patients, particularly when the lead 16 is positioned substernally as shown in FIG. 2A.

R-wave sensing threshold 110 is held at the second threshold value 118 until the expiration of drop time interval 136. Drop time interval 136 may be started at the time R-wave 104 is sensed, as shown in FIG. 5, or upon expiration of blanking interval 130, blanking interval 132, or sense delay interval 134. When drop time interval 136 is started upon sensing R-wave 104, it may be set to 1.5 seconds or other relatively long interval to promote a high likelihood of maintaining the R-wave sensing threshold at the second value 118 until after P-wave 108, or at least until after the peak amplitude or majority of P-wave 108. Drop time interval 136 may be a fixed interval or may be programmable by the user. The drop time interval 136 may range from 0.8 to 2.0 seconds in other examples. In some examples, the drop time interval 136 may be adjusted with changes in heart rate. For example, as heart rate increases based on measurements of RR intervals such as RR interval 140, the drop time interval 136 may be shortened. As heart rate decreases, the drop time interval 136 may be increased.

The second threshold value 118 is shown to be a constant value from the expiration of sense delay interval 134 until the expiration of drop time interval 136. In other examples, the second threshold value 188 may slowly decay until the expiration of drop time interval 136. The decay rate would be selected to be slow, however, so that the ending R-wave sensing threshold at the expiration of the drop time interval 136 is still expected to be greater than the P-wave amplitude to avoid P-wave oversensing. An example decay rate might be 10% of the maximum peak amplitude 112 per second.

If the cardiac electrical signal has not crossed R-wave sensing threshold 110 prior to expiration of the drop time interval 136, the R-wave sensing threshold 110 is adjusted from the second sensing threshold value 118 to a minimum sensing threshold value 120, which may be referred to as the "sensing floor." The R-wave sensing threshold 110 remains at the minimum sensing threshold 120 until the cardiac electrical signal 102 crosses the threshold 120. In the example shown, R-wave 104' is sensed when the minimum sensing threshold 120 is crossed, causing sensing circuit 86 to generate R-wave sensed event signal 152.

In some examples, the minimum sensing threshold value 120 is set equal to the programmed sensitivity setting 122 which may be, for example, 0.07 millivolts (mV), 0.15 mV, 0.3 mV, 0.6 mV or higher. The programmed sensitivity setting 122 may establish the minimum possible sensing threshold value in some examples, in which case the R-wave sensing threshold 110 is never set below the programmed sensitivity setting 122. The sensitivity setting 122 may be programmable between 0.075 and 1.2 millivolts (mV) in one example and may be selected by a user as the minimum voltage threshold required to sense a cardiac event from cardiac signal 102. As the value of the sensitivity setting 122 decreases, sensitivity of the sensing circuit for sensing low amplitude signals increases. As such, a low sensitivity setting 122 corresponds to high sensitivity for sensing R-waves. The lowest setting, e.g., 0.07 mV, corresponds to the highest sensitivity, and the highest setting, e.g., 1.2 mV, corresponds to the lowest sensitivity of sensing circuit 86 for sensing R-waves.

Pulses of the cardiac electrical signal 102 that have a maximum peak voltage below the programmed sensitivity setting 122 are considered noise or events that are not intended to be sensed, which may include T-waves and P-waves. When T-wave or P-wave sensing is detected or observed, the user may reprogram the sensitivity setting 122 to a higher setting (lower sensitivity). However, by providing the multi-threshold R-wave sensing threshold 110, controlled using a programmable sense delay time interval 134 and drop time interval 136, the programmed sensitivity setting 122 may be kept at a low value to provide high sensitivity for sensing R-waves and low amplitude fibrillation waves while still minimizing the likelihood of T-wave and P-wave oversensing.

In addition to determining the starting threshold value 116 and the second threshold value 118, control circuit 80 may establish a maximum R-wave sensing threshold limit 114 that limits the maximum starting value of R-wave sensing threshold 110. If the starting value 116 of the R-wave sensing threshold 110 determined based on peak amplitude 112 of R-wave 104 is greater than the maximum threshold limit 114, the starting value of R-wave sensing threshold 110 may be set to the maximum threshold limit 114. In some cases, a maximum R-wave sensing threshold limit 114 is set as a fixed multiple or fixed gain of the programmed sensitivity setting 122, for example a gain of eight to ten times the sensitivity setting 122. In other examples, the gain applied to the programmed sensitivity setting 122 for establishing a maximum R-wave sensing threshold limit 114 is a variable gain. The variable gain may be defined to be dependent on the programmed sensitivity setting 122 as described below.

Figure 6:
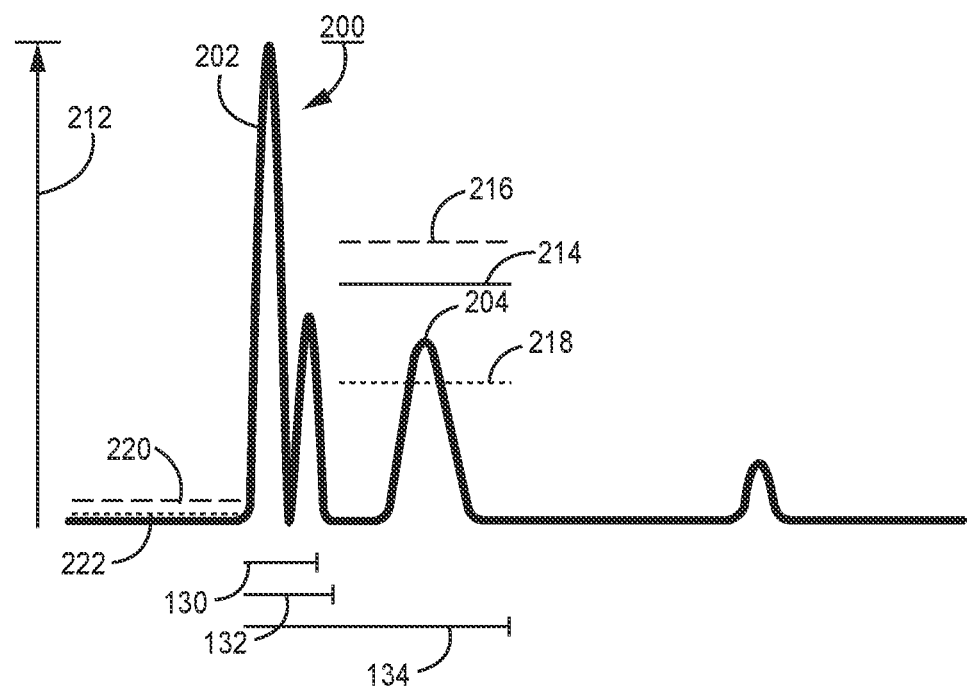
FIG. 6 is a diagram of a filtered and rectified cardiac electrical signal and a maximum sensing threshold limit according to one example.

FIG. 6 is a diagram of a filtered and rectified cardiac electrical signal 200 including R-wave 202 and T-wave 204. Two examples of maximum R-wave sensing threshold limits 216 and 218 are each set as a fixed multiple of a respective programmed sensitivity setting 220 or 222. As can be seen in this example, in some cases, when large amplitude R-waves and T-waves occur, the maximum R-wave sensing threshold limit 218 set as a fixed multiple of the lower programmed sensitivity setting 222 may result in T-wave oversensing because T-wave 204 crosses the maximum R-wave sensing threshold limit 218. In an illustrative example, the maximum peak amplitude 212 of R-wave 202 is 10 mV, and the sensitivity setting 222 is programmed to 0.3 mV. The maximum R-wave sensing threshold limit 218 is set to 3 mV, when a fixed gain of 10 times the programmed sensitivity setting is used to set the maximum threshold limit 218. In this situation of a very large R-wave 202, the first sensing threshold value 214 determined as a percentage (50% in the example shown) of the maximum peak amplitude 212 of the R-wave 202 is greater than the maximum sensing threshold limit 218. As such, the R-wave sensing threshold is set to the maximum sensing threshold limit 218 at the expiration of the second blanking interval 132 until the expiration of sense delay interval 134. The R-wave sensing threshold set to the maximum threshold limit 218 would result in T-wave oversensing in this example since the maximum limit 218 is less than the amplitude of T-wave 204.

In order to prevent T-wave oversensing, a higher sensitivity setting 220 could be programmed, for example 0.6 mV. The maximum sensing threshold limit 216 is 6 mV in the example of the programmed sensitivity setting 220 being 0.6 mV and a fixed gain of 10 being used to determine the maximum limit 216. This maximum threshold limit 216 is greater than the starting sensing threshold value 214 determined as a percentage of R-wave amplitude peak 212, which is 50% of 10 mV or 5 mV in this example. This starting threshold value 214 is applied as the R-wave sensing threshold upon expiration of the second blanking interval 132 since it is less than the maximum threshold limit 216. The starting threshold value 214 does not result in T-wave oversensing because the amplitude of T-wave 204 is less than the starting sensing threshold value 214.

As can be seen by the illustrative example of FIG. 6, in the presence of large amplitude R-waves and T-waves, T-wave oversensing can occur when a maximum sensing threshold limit is determined as a fixed gain of the sensitivity setting and the sensitivity setting is low. In order to avoid T-wave oversensing, the sensitivity setting can be increased to lower the sensitivity, e.g., to 0.6 mV from 0.3 mV as represented by sensitivity setting 220 and sensitivity setting 222, respectively, in FIG. 6. The higher sensitivity setting, however, makes sensing circuit 86 less sensitive to low amplitude R-waves that may occur during VT or VF, potentially resulting in under-detection of ventricular tachyarrhythmia episodes.

Figure 7:
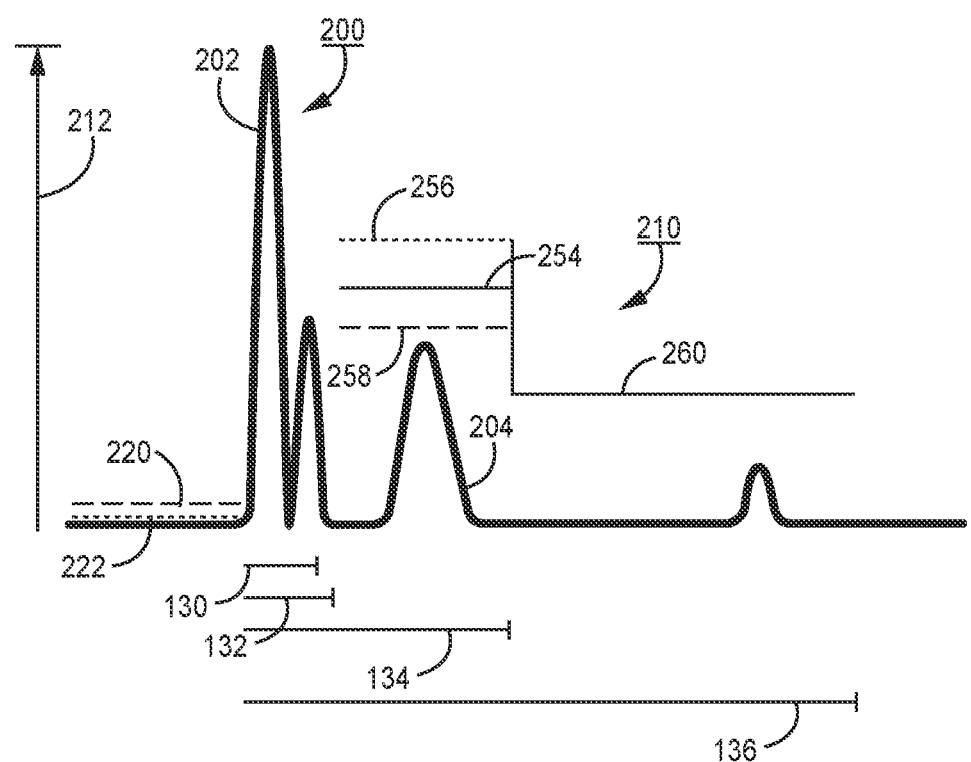
FIG. 7 is a diagram of the cardiac electrical signal shown in FIG. 6 and maximum sensing threshold limits determined based on a variable, sensitivity-dependent gain.

FIG. 7 is a diagram of the cardiac electrical signal 200 shown in FIG. 6 shown with two different examples of maximum sensing threshold limits 256 and 258 determined using a variable, sensitivity-dependent gain applied to the programmed sensitivity. The gain or multiple of the programmed sensitivity setting used by control circuit 80 to determine the maximum sensing threshold limit following a sensed event is a function of the programmed sensitivity setting in some examples. The maximum sensing threshold limit may be inversely related to the programmed sensitivity setting such that a higher gain is applied to a lower programmed sensitivity setting for obtaining the maximum threshold limit.

For instance, control circuit 80 may compute a variable gain (G) for determining a maximum sensing threshold limit by determining an inverse proportion of the sensitivity setting and adding a constant using the equation $G=A+B/S$ where A and B are constants and S is the programmed sensitivity (B/S being an inverse proportion of the programmed sensitivity setting). In some examples, the gain determined for each available programmable sensitivity setting is stored in a look-up table in memory 80 and is retrieved by control circuit 80 each time a new sensitivity setting is programmed.

In one example, A is at least 5 and B is at least 1.5. For instance, A may be equal to 6 and B may be equal to 2.5 in the equation given for the gain G above. The minimum possible value of the maximum sensing threshold limit will approach 2.5 since the maximum sensing threshold limit is the product of the gain and the programmed sensitivity setting, or $6S+2.5$ where S equals the programmed sensitivity setting. For a programmable range of sensitivity settings from 0.075 mV to 1.2 mV, the sensitivity-dependent gain ranges from approximately 39.3 for the lowest sensitivity setting of 0.075 mV (corresponding to highest sensitivity) to approximately 8.1 for the highest sensitivity setting of 1.2 mV (corresponding to the lowest sensitivity). The higher the sensitivity, i.e., the lower the sensitivity setting, the higher the sensitivity-dependent gain is.

For a programmed sensitivity of 0.3 mV, the sensitivity-dependent gain is given by $G=6+2.5/0.3$ or approximately 14.3 using the constants given in the foregoing example. The maximum sensing threshold limit 258 determined when the sensitivity setting 222 is programmed to 0.3 mV is the sensitivity-dependent gain, 14.3, multiplied by the sensitivity setting, 0.3 mV, or approximately 4.3 mV. This maximum sensing threshold limit 258 is less than the first sensing threshold value 254 determined as a percentage (50% in this example) of R-wave peak amplitude 212. As a result, the R-wave sensing threshold 210 will be set to the maximum sensing threshold limit 258, but in this case the sensing threshold limit 258 set using the variable gain is greater than the amplitude of T-wave 204, thereby avoiding T-wave oversensing while still allowing a high sensitivity (low sensitivity setting) to be used for sensing low amplitude waveforms during VT or VF (especially spontaneous fine VF) after the drop time interval 134 expires.

Continuing with the illustrative example given above, the maximum sensing threshold limit 256 determined for a programmed sensitivity setting of 0.6 mV 220 is determined using a sensitivity-dependent gain of approximately 10.2 ($G=6+2.5/0.6$). The maximum sensing threshold limit 256 is 6.1 mV in this case (0.6 mV multiplied by the gain of 10.2), which is greater than the starting sensing threshold value 254 determined as a percentage (e.g., 50%) of the R-wave peak amplitude 212. In this case, the R-wave sensing threshold 210 is set to the starting sensing threshold value 254 at the expiration of the second blanking interval 132 (shown in FIG. 5).

In both cases of 0.6 mV sensitivity setting 220 and 0.3 mV sensitivity setting 222, the R-wave sensing threshold value during the sense delay interval 134 avoids T-wave oversensing in the presence of large amplitude R-waves and T-waves. Even when a low sensitivity setting is used, e.g., 0.3 mV or less, so that sensing circuit 86 remains highly sensitive to small R-waves that may occur during a ventricular tachyarrhythmia, T-wave oversensing is avoided by using a sensitivity-dependent variable gain for determining the maximum R-wave sensing threshold limit.

At the expiration of the sense delay interval 134, the R-wave sensing threshold is adjusted from the starting threshold 254 or 258, to the second threshold 260 which is determined as 25% of the R-wave peak amplitude 212 in this example. The second threshold 260 remains in effect until the drop time interval 136 expires (described in FIG. 5) after which the R-wave sensing threshold 210 drops to the programmed sensitivity setting, either the 0.6 mV sensitivity setting 220 or the 0.3 mV sensitivity setting 222 in the example shown in FIG. 7.

Figure 8A:
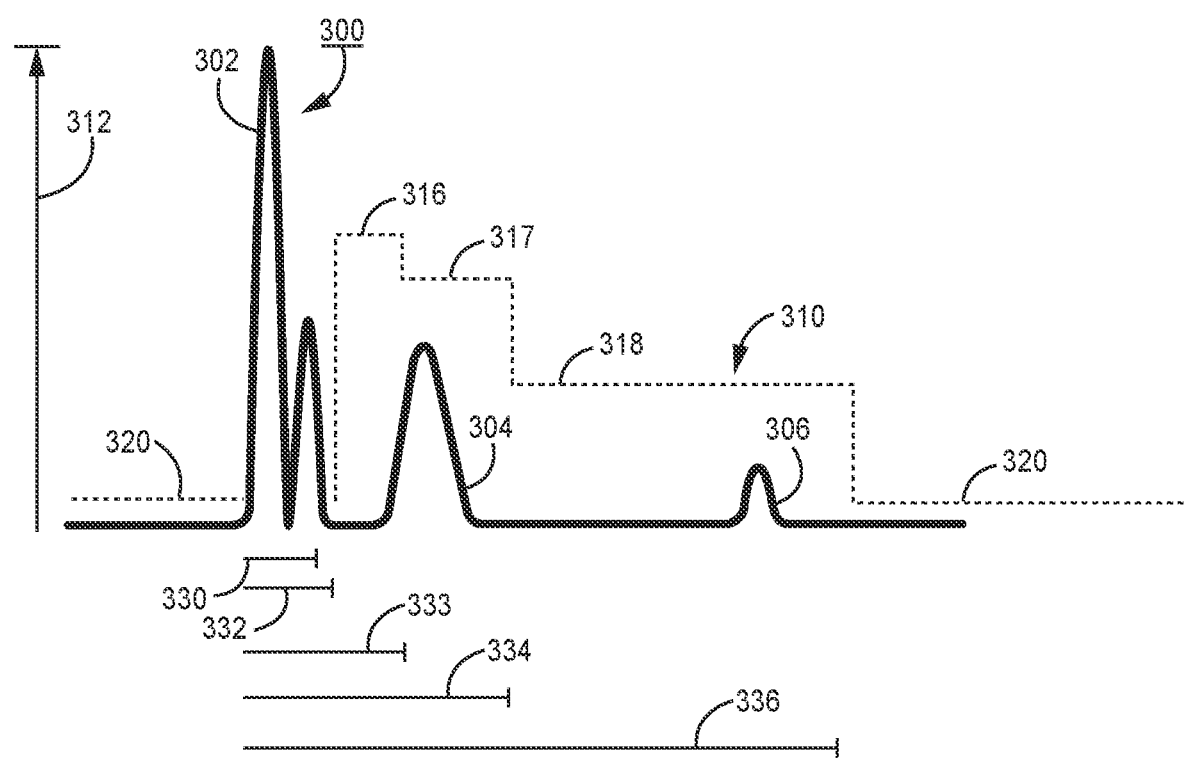
FIG. 8A is a diagram of a multi-level R-wave sensing threshold according to another example.

FIG. 8A is a diagram of a filtered and rectified cardiac electrical signal 300 including an R-wave 302, a T-wave 304, and a P-wave 306 and an automatically adjusted R-wave sensing threshold 310 having multiple sensing threshold values 316, 317, 318 and 320. In the examples of FIGS. 5, 6 and 7, the R-wave sensing threshold 310 is set to the first, starting threshold value and second threshold value before dropping to the programmed sensitivity setting. In other examples, the R-wave sensing threshold 310 may be adjusted to three or more threshold values before dropping to the programmed sensitivity setting.

As shown in FIG. 8A, the starting threshold value 316 may be determined as a first percentage of the peak R-wave amplitude 312 that is detected during first blanking interval 330, e.g., 62.5% or between 55% and 70% of the peak R-wave amplitude 312. The starting threshold value 316 may be maintained from the expiration of the second blanking interval 332 until the expiration of a first sense delay interval 333. The first sense delay interval 333 may be approximately 180 ms, for example 30 to 60 ms longer than the second blanking interval 332. The higher starting threshold value 316 applied for a short interval may reduce the likelihood of double sensing the R-wave 302, particularly in patients exhibiting a wide QRS complex.

Upon expiration of the first sense delay interval 333, the R-wave sensing threshold 310 is adjusted to a lower, second sensing threshold value 317, which may be between 30% and 60% of the R-wave peak amplitude 312, such as 50% of the R-wave peak amplitude 312. The second sensing threshold value 317 is maintained until expiration of the second sense delay interval 334, which may be between 300 and 360 ms, and may be set equal to a programmed TDI as described previously in conjunction with FIG. 5.

Upon expiration of the second sense delay interval 334, the third sensing threshold value 318 is applied until a drop time interval 336 expires, and the R-wave sensing threshold 310 falls to a minimum sensing threshold value 320, which may be equal to the programmed sensitivity setting. The third sensing threshold value 318 may be approximately 28% of the R-wave peak amplitude 312, or between 20% and 30% in other examples, and extend for a drop time interval 336 of one to two seconds, e.g., 1.5 seconds.

Figure 8B:
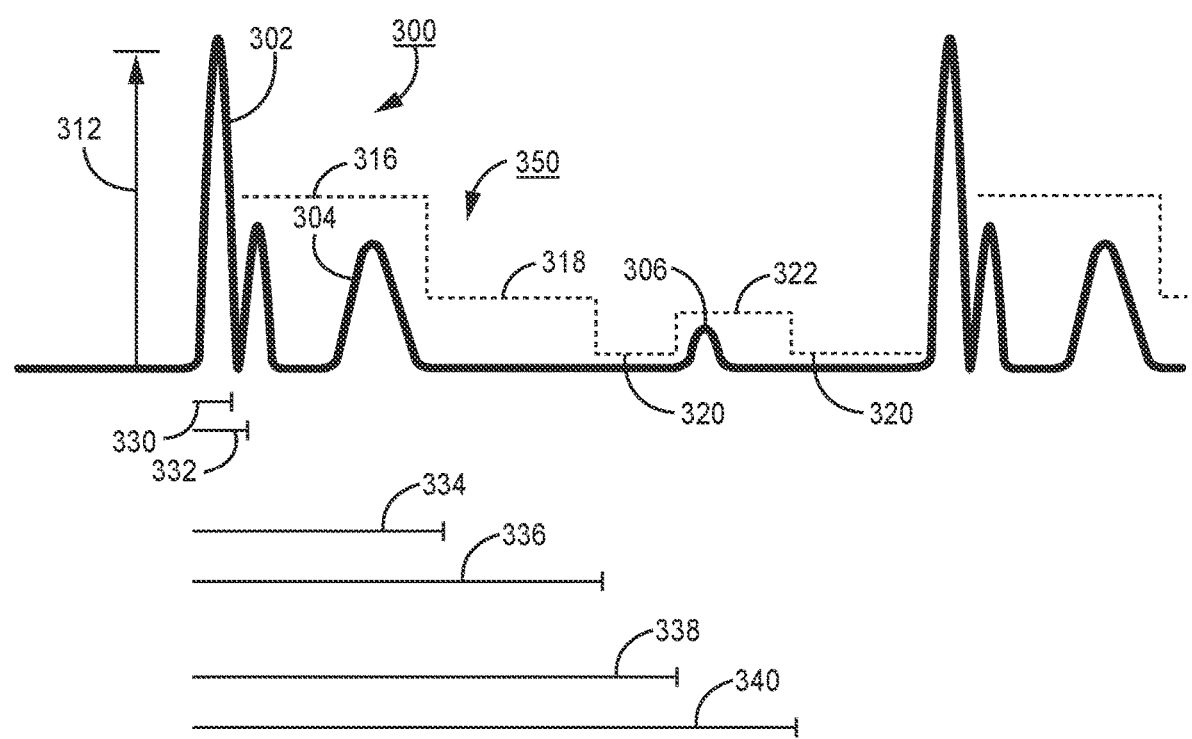
FIG. 8B is a diagram of a non-monotonic, multi-level R-wave sensing threshold according to another example.

FIG. 8B is a diagram of a non-monotonic, multi-level R-wave sensing threshold 350 according to another example. In the examples of FIGS. 5 and 8A, R-wave sensing threshold 110 and R-wave sensing threshold 310, respectively, are monotonically decreasing sensing thresholds. In other examples, the multi-level R-wave sensing threshold controlled by control circuit 80 is non-monotonic, including one or more step increases in the value of R-wave sensing threshold in addition to the decreasing step changes in the R-wave sensing threshold value.

The filtered and rectified cardiac electrical signal 300, including R-wave 302, T-wave 304, and P-wave 306, and an automatically adjusted R-wave sensing threshold 350 are shown in FIG. 8B. R-wave sensing threshold 350 may include a starting sensing threshold value 316 beginning upon expiration of second blanking interval 332 and a second sensing threshold value 318 beginning after expiration of the sense delay interval 334. R-wave sensing threshold 350 drops to the programmed sensitivity setting 320 upon expiration of drop time interval 336.

If cardiac signal 300 does not cross the R-wave sensing threshold 350 before a maximum sensitivity interval 338 expires, the R-wave sensing threshold 350 is increased to a third sensing threshold value 322. The third sensing threshold value may be equal to the second sensing threshold value 318 or set as a percentage of a previously determined baseline P-wave maximum peak amplitude, e.g., 1.5 times a previously determined P-wave maximum peak amplitude. The maximum sensitivity interval 338 controls how long the R-wave sensitivity threshold 350 is held at the maximum sensitivity, e.g., the programmed sensitivity setting 320, before being increased to the third sensing threshold value 322. In some examples, the maximum sensitivity interval 338 is approximately 200 ms longer than the drop time interval 336 so that the R-wave sensing threshold 350 is set to the programmed sensitivity setting 320 for up to 200 ms if an R-wave sensing threshold crossing does not occur.

Upon expiration of the maximum sensitivity interval 338, R-wave sensing threshold 350 is increased to the third sensing threshold value 322 to minimize the likelihood of oversensing the P-wave 306 during very slow heart rates and when the P-wave 306 has an amplitude greater than the programmed sensitivity setting 320. By allowing the R-wave sensing threshold 350 to drop to the programmed sensitivity setting 320, to provide high sensitivity for up to a predefined time interval as controlled by interval 338, undersensing of low amplitude, fine VF waveforms is avoided. Sensing circuit 86 may sense low amplitude ventricular tachyarrhythmia waveforms after expiration of drop time interval 336 and before expiration of maximum sensitivity interval 338. If the heart rate is very slow, however, such that the P-wave 306 arrives relatively late after R-wave 302 and after expiration of drop-time interval 336, P-wave oversensing may be avoided by increasing the R-wave sensing threshold 350 to the third threshold value 322 while still providing an interval of high sensitivity to low amplitude tachyarrhythmia waveforms. The third sensing threshold value 322 may be maintained until a sensing threshold crossing occurs. In other examples, as shown in FIG. 8B, the third sensing threshold value 322 is held until a second drop time interval 340 expires, at which time the R-wave sensing threshold 350 is adjusted back to the programmed sensitivity setting 320.

Figure 9:
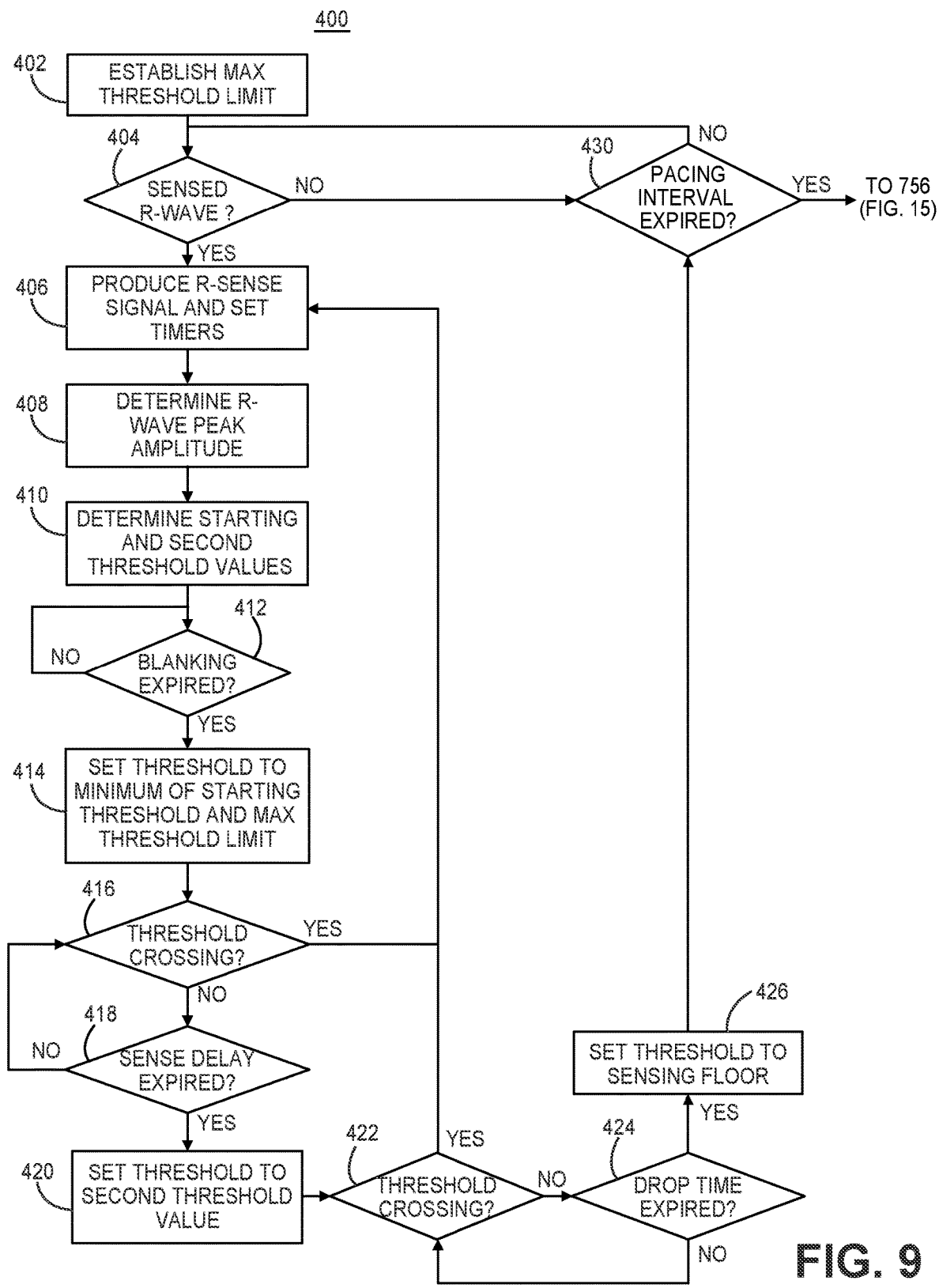
FIG. 9 is a flow chart of a method performed by the ICD of FIGS. 1A-2C for controlling the R-wave sensing threshold according to one example.

FIG. 9 is a flow chart 400 of a method for controlling the R-wave sensing threshold according to one example. At block 402, the control circuit 80 establishes the maximum threshold limit. The maximum threshold limit may be set based on a sensitivity-dependent gain as described in conjunction with FIG. 7. Control circuit 80 determines the sensitivity-dependent gain then computes the maximum threshold limit as the product of the gain and the programmed sensitivity setting. Alternatively, the maximum threshold limit may be set as a fixed multiple of the programmed sensitivity setting, using a gain that is independent of the programmed sensitivity, as described in conjunction with FIG. 6. The maximum threshold limit is re-established at block 402 each time the sensitivity is reprogrammed to a different sensitivity setting.

At block 404, an R-wave is sensed in response to the cardiac electrical signal crossing the R-wave sensing threshold, which may initially be set to the maximum sensing threshold, a nominal sensing threshold, the programmed sensitivity setting or other starting value. In response to sensing an R-wave, sensing circuit 86 produces an R-wave sensed event signal at block 408, and control circuit 80 sets various timers or counters as described in conjunction with FIGS. 5 and 8A and 8B for controlling the multi-threshold R-wave sensing threshold. For example, a first blanking interval, which may be a hardware controlled blanking interval, a second blanking interval, which may be a digital blanking interval controlled by firmware stored in memory 82, a sense delay interval, a drop time interval, and a maximum sensitivity interval may be started upon sensing an R-wave due to a positive-going R-wave sensing threshold crossing of the cardiac electrical signal received by sensing circuit 86.

At block 408, the maximum peak amplitude of the sensed R-wave is determined during the first post-sense blanking interval. The R-wave peak amplitude may be determined by a peak track and hold circuit or other hardware or firmware. The R-wave peak amplitude is fetched by control circuit 80 at the expiration of the first post-sense blanking interval. Control circuit 80 determines the starting and second threshold values at block 410 as two different percentages of the R-wave peak amplitude. For example, the starting threshold value may be determined as 40 to 60% of the R-wave peak amplitude, and the second threshold value may be determined as 20 to 30% of the R-wave peak amplitude. Control circuit 80 may execute firmware after expiration of the first blanking interval for determining the starting, first threshold value and the second threshold value before expiration of the second blanking interval. The starting and second threshold values may be passed to sensing circuit 86 as control values used by circuitry of sensing circuit 86 for controlling the R-wave sensing threshold. In other examples, three or more threshold values are determined as described in conjunction with FIGS. 8A and 8B.

Upon expiration of the second blanking interval, as determined at block 412, the sensing circuit 86 sets the starting R-wave sensing threshold at block 414 to the starting threshold value determined as a percentage of the R-wave peak amplitude or to the maximum threshold limit, whichever is less, under the control of control circuit 80. If the cardiac electrical signal crosses the starting R-wave sensing threshold, as determined at block 416, the process returns to block 406 where sensing circuit 86 produces another R-wave sensed event signal and restarts the various control time intervals as described above, e.g., first post-sense blanking interval 130, second post-sense blanking interval 132, sense delay interval 134 and drop time interval 136 shown in FIG. 5.

If the sense delay interval expires at block 418 before the cardiac electrical signal crosses the R-wave sensing threshold, sensing circuit 86 adjusts the R-wave sensing threshold at block 420 to the second threshold value received from control circuit 80. If the cardiac electrical signal crosses the R-wave sensing threshold adjusted to the second threshold value, as determined at block 422, the process returns to block 406 to generate an R-wave sensed event signal and reset the control time intervals as described above. If the drop time interval expires at block 424 without the cardiac electrical signal crossing the R-wave sensing threshold (block 422), the sensing circuit 86 adjusts the R-wave sensing threshold to the minimum threshold value or sensing floor, which may be the programmed sensitivity setting, at block 426. In other examples, more than two drop steps in the sensing threshold value may be implemented, as described in conjunction with FIG. 8A, and/or a step increase in the sensing threshold value may be included as described in conjunction with FIG. 8B.

Sensing circuit 86 waits for the cardiac electrical signal to cross the sensing floor at block 404 and the process repeats by advancing to block 406 if the cardiac electrical signal crosses the sensing floor. If a cardiac electrical stimulation therapy is enabled, however, for example a cardiac pacing therapy, the control circuit 80 may start a pacing interval at block 406 when various timers are set in response to the R-wave sensed event signal. If the pacing interval expires at block 430 before the cardiac electrical signal crosses the R-wave sensing threshold, control circuit 80 may advance to block 756 of FIG. 15, described below, to deliver a cardiac pacing pulse and control the R-wave sensing threshold according to post-pace R-wave sensing control parameters.

While not shown in FIG. 9, it is recognized that a pacing interval may expire during the sense delay interval (e.g., an ATP pulse) or the drop time interval (e.g., a rate responsive pacing pulse) or any time prior to an R-wave sensing threshold crossing causing a pacing pulse to be delivered. Control circuit 80 may operate according to the methods described in conjunction with FIG. 15 for controlling the R-wave sensing threshold post-pulse. The various timing intervals and threshold values shown in any of FIGS. 5-8B may be determined and applied for controlling the R-wave sensing threshold following a delivered electrical stimulation pulse and are not limited to being used following only intrinsic R-wave sensed events. However, control parameters used to control the R-wave sensing threshold following an electrical stimulation pulse may be different than the post-sense R-wave sensing threshold control parameters described in conjunction with FIGS. 5-9. Examples of post-pulse R-wave sensing threshold control parameters are described in conjunction with FIGS. 14-16 below.

Furthermore, while the techniques have been described for controlling an R-wave sensing threshold for sensing R-waves attendant to ventricular depolarization, it is to be understood that aspects of the disclosed techniques may be used for controlling a cardiac event sensing threshold for sensing other cardiac event signals, such as P-waves attendant to atrial depolarization or T-waves attendant to ventricular repolarization. For example, a maximum P-wave sensing threshold limit may be set based on a sensitivity-dependent gain and a programmed sensitivity; a maximum T-wave sensing threshold limit may be set based on a sensitivity-dependent gain and programmed sensitivity. P-wave and/or T-wave sensing thresholds may be controlled using multiple threshold levels and multiple time intervals.

Figure 10:
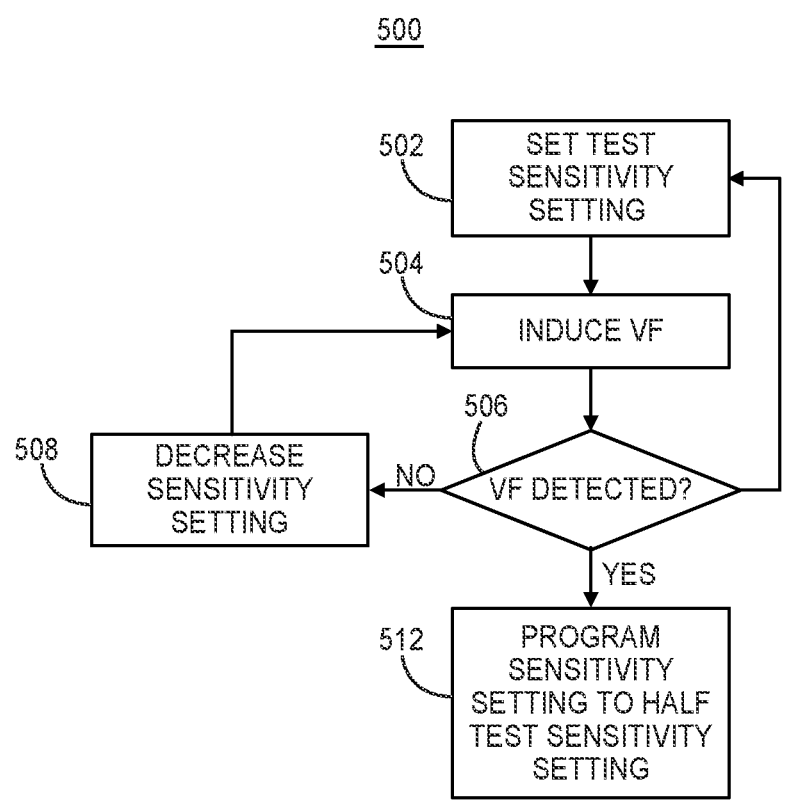
FIG. 10 is a flow chart of a method for selecting a sensitivity setting in the ICD system of FIGS. 1A-2C according to one example.

FIG. 10 is a flow chart of a method for selecting a sensitivity setting in ICD 14. The process shown in FIG. 10 may be performed at the time of ICD 14 implant or during a lead replacement procedure to determine a reliable sensitivity setting for detecting low amplitude fibrillation waves during VF. The process shown by flow chart 500 may be a semi-automated process executed by ICD 14 in response to programming commands received from external device 40.

At block 502, a test sensitivity setting is selected. The test sensitivity setting may be programmed by a user using external device 40 or may be a value two times a nominal sensitivity setting or a preferred sensitivity setting, which may be based on a measured R-wave amplitude. For example, if the R-wave amplitude observed on an electrocardiogram signal produced by ICD 14 and transmitted to external device 40 is at least 3 mV, a test sensitivity setting of 0.6 mV may be set at block 502 for a preferred sensitivity setting of 0.3 mV, half of the test setting.

At block 504, a user transmits a VF induction command to ICD 14 using external device 40. ICD 14 may induce VF using any implemented induction method, such as a T-shock, which is a large energy electrical pulse delivered during the vulnerable period associated with the T-wave. If VF is detected at the programmed sensitivity setting, "Yes" branch of block 506, a defibrillation shock is delivered according to programmed shock therapy control parameters to terminate the VF. If VF is not detected at the programmed sensitivity within a predetermined time limit, a shock is delivered to terminate the induced VF, and the sensitivity setting may be decreased, to increase the sensitivity to VF waveforms, at block 508. VF may be induced again at block 506 to test the new sensitivity setting. This process may be repeated one or more times as needed to determine the highest sensitivity setting that allows successful detection of VF. Alternatively, if VF is not detected at block 506 using the first sensitivity setting, a recording of the cardiac electrical signal during the induced VF may be used to determine the voltage amplitude of the VF waveforms, and the sensitivity setting may be programmed lower than the VF waveform amplitude at block 512. In still other examples, if sensing circuit 86 includes two sensing channels, the cardiac electrical signal may be sensed using two different test sensitivity settings simultaneously to determine if one or both result in VF detection.

When VF is detected at the current test sensitivity setting, the sensitivity setting is programmed to one-half to one-third the test sensitivity setting. For example, if the sensitivity setting tested is 0.6 mV, the sensitivity setting is programmed to 0.3 mV at block 512. By using a sensitivity-dependent gain for setting the maximum R-wave sensing threshold limit, a lower sensitivity setting may be used with confidence in avoiding T-wave and P-wave oversensing while still providing high sensitivity for detecting VF, both acutely and chronically after implantation of the ICD system 10.

The R-wave amplitude of the cardiac electrical signal received by the extra-cardiovascular electrodes is similar during the acute phase (days or weeks) after implantation and after chronic implantation (months or years). Accordingly, the recommended sensitivity setting determined at block 512 need not change based on time since implant, unlike transvenous ICD systems which may have larger R-wave amplitude acutely and smaller R-wave amplitude chronically. A two-fold or three fold sensitivity safety margin (in other words using one-half to one-third of a tested sensitivity setting) may be used in the extra-cardiovascular ICD system 10 rather than higher safety margins which have been practiced in the past for transvenous ICD systems, such as a four-fold safety margin. Control of the R-wave sensing threshold as disclosed herein using a two- to three-fold sensitivity safety margin minimizes the risk of undersensing spontaneous fine VF (usually with small waveform amplitudes) while avoiding T-wave and P-wave oversensing.

Figure 11:
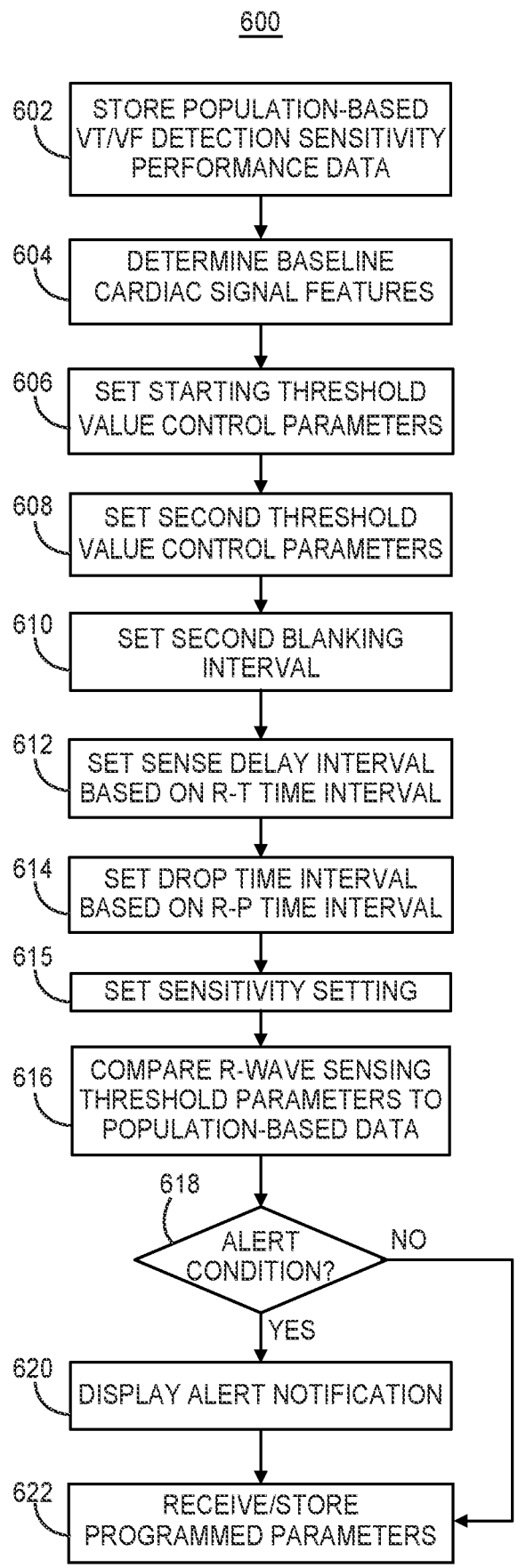
FIG. 11 is a flow chart of a method for selecting R-wave sensing threshold control parameters according to one example.

FIG. 11 is a flow chart 600 of a method for selecting R-wave sensing threshold control parameters according to one example. As described above in conjunction with FIG. 10, the sensitivity setting, which may define the minimum R-wave sensing threshold value, may be based at least in part on VF detection testing. The starting value of the R-wave sensing threshold may be set on a beat-by-beat basis based on the peak R-wave amplitude (as shown in FIG. 5) or based on the programmed sensitivity following an electrical stimulation pulse as described below in conjunction with FIG. 14. The gain applied to the sensitivity for setting the maximum R-wave sensing threshold value may be a variable gain that is dependent on the programmed sensitivity setting as described in conjunction with FIG. 7. In addition to these R-wave sensing threshold control parameters, other R-wave sensing threshold control parameters may be variable and/or programmable based on cardiac signal features determined for an individual patient to tailor optimal R-wave sensing threshold control for that patient and/or based on empirical data from a population of patients.

For example, the percentage of the R-wave peak amplitude used to set the post-sense starting threshold value 116, the second blanking interval 132, the sense delay interval 134, the post-sense second, lower threshold value 118, and the drop time interval 136 (all shown in FIG. 5) may all be programmable or variable values that may be tailored to an individual patient and/or based on sensitivity performance data obtained from a population of patients. Other control parameters such as a second sensing delay interval 334 as shown in FIG. 8A or a maximum sensitivity interval 338 as shown in FIG. 8B may also be programmable and tailored individually to a patient.

At block 602, population-based VT/VF detection sensitivity for one or more individual R-wave sensing threshold control parameter settings and/or combinations of R-wave sensing threshold control parameter settings may be stored in ICD memory 82 and/or in memory 53 of external device 40. For example, a VT/VF detection sensitivity curve as a function of the programmed sensitivity setting 122 (FIG. 5), second blanking interval 132, drop time interval 136, or other R-wave sensing control parameters described above may be determined from empirical data gathered from a population of ICD patients.

Figure 12:
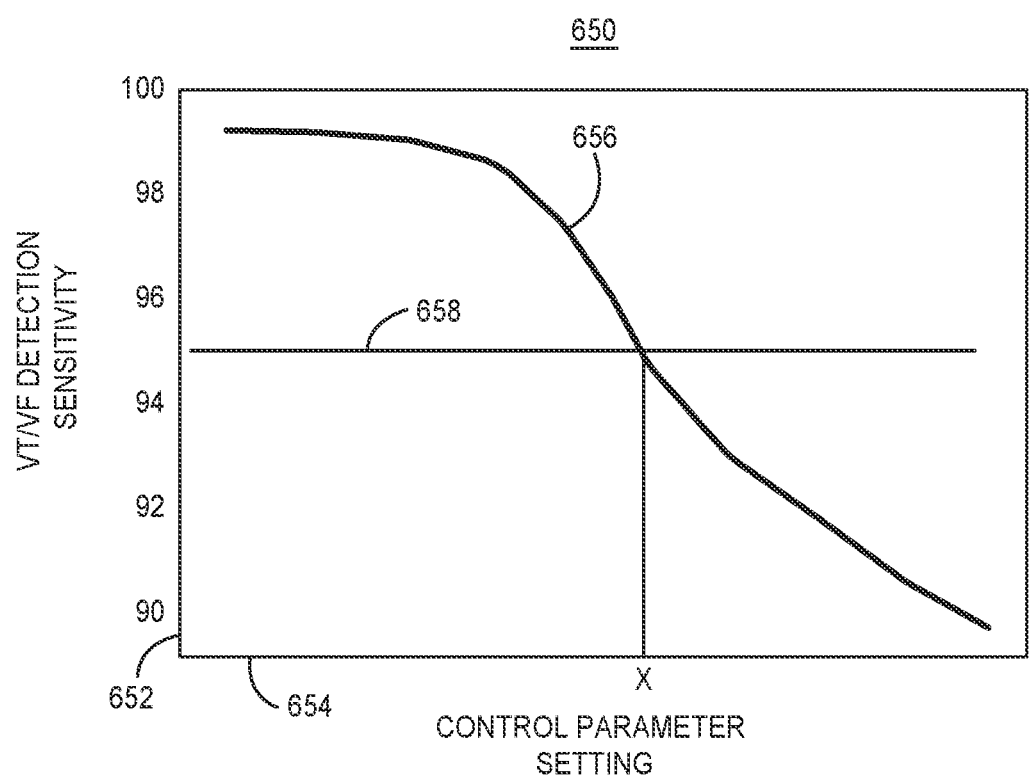
FIG. 12 is a plot of an example of a ventricular tachycardia/ventricular fibrillation (VT/VF) detection sensitivity curve.

FIG. 12 is a plot 650 of an illustrative VT/VF detection sensitivity curve 656. VT/VF detection sensitivity, expressed as the percentage of all VT/VF episodes actually detected, is plotted along the y-axis 652 as a function of an R-wave sensing threshold control parameter setting plotted along the x-axis 654. The sensing control parameter is indicated generically in FIG. 12 but may be the second blanking interval 132, the percentage used to determine the starting value 116 of the R-wave sensing threshold, the sense delay interval 134, the percentage used to determine the second value 118 of the R-wave sensing threshold, the drop time interval 136, the sensitivity setting 122 (all shown in FIG. 5) or any of the other R-wave sensing threshold control parameters described herein.

An alert threshold 658 may be set, below which the VT/VF detection sensitivity falls below VT/VF detection performance expectations, e.g., 95%. When the control parameter setting has a programmed value greater than "X", the VT/VF detection sensitivity falls below the alert threshold 658. As described below, stored VT/VF detection sensitivity data may be used by control circuit 80 (or external device processor 52) to look up an expected VT/VF detection sensitivity for a programmed R-wave sensing threshold control parameter individually or in combination with other parameter values in a multi-parameter n-dimensional model of detection sensitivity. If the detection sensitivity falls below an alert threshold 658 for ICD performance expectations, a clinician alert may be generated as described below.

Figure 13:
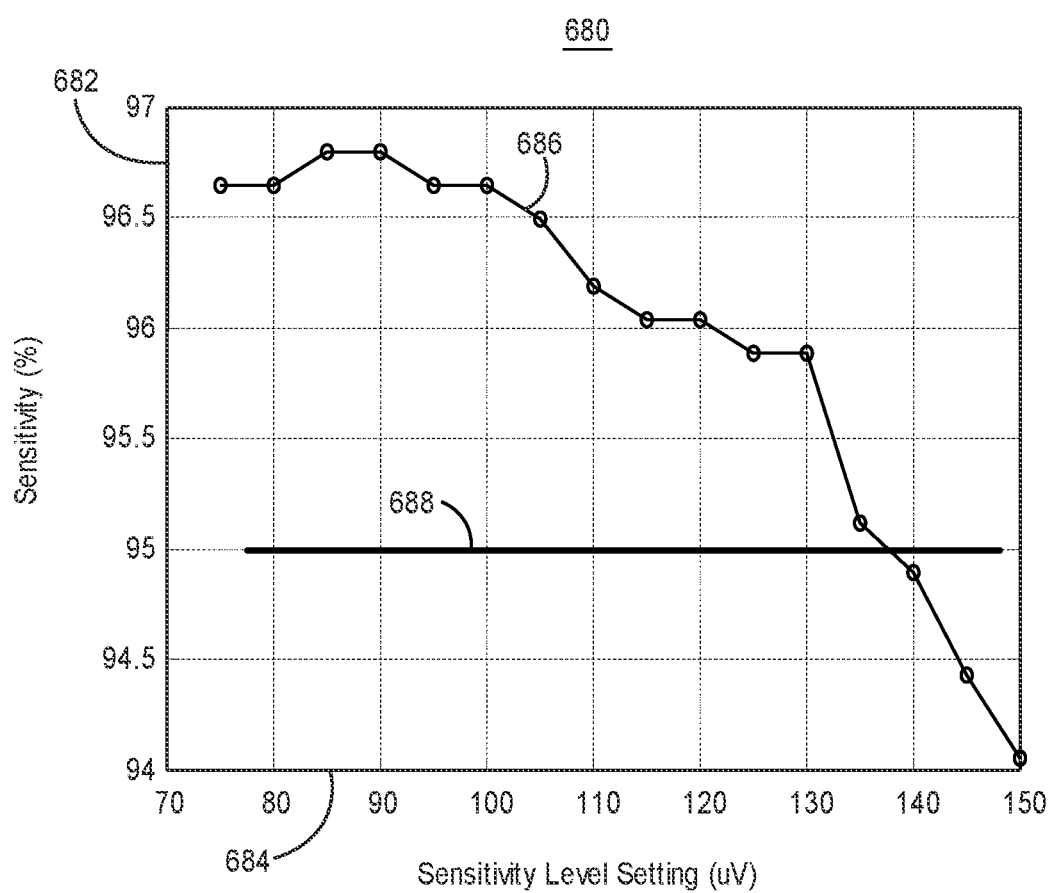
FIG. 13 is a plot of a VT/VF detection sensitivity curve as a function of the programmed sensitivity setting.

FIG. 13 is a plot 680 of an example VT/VF detection sensitivity curve 686. VT/VF detection sensitivity is plotted along y-axis 682 as a function of the programmed sensitivity setting plotted along x-axis 684. When the programmed sensitivity setting is less than approximately 135 microvolts, the VT/VF detection sensitivity is greater than the alert threshold 688, shown as 95% in this example though other alert threshold levels may be selected. In this example, when the programmed sensitivity setting is 140 microvolts or higher, the VT/VF detection sensitivity 686 falls below the alert threshold 688, and the ICD system 10 may generate an alert displayed on external device display 54 as described below in response to a sensitivity setting greater than 140 microvolts being selected for programming.

FIGS. 12 and 13 represent VT/VF detection sensitivity as a function of a single sensing threshold control parameter setting. It is recognized that instead of a single parameter function as shown in FIG. 12, VT/VF sensitivity may be modeled in a multi-parameter, n-dimensional model taking into account a combination of sensing threshold parameters. Furthermore, it is contemplated that instead of sensitivity or in addition to sensitivity, VT/VF detection specificity may be modeled for one or more sensing threshold parameters, individually or in a multi-parameter, n-dimensional model. Sensing threshold control parameters may be determined based on baseline cardiac electrical signal features and selected in order to achieve a targeted specificity and/or targeted sensitivity.

Returning to FIG. 11, at block 604, a processor included in control circuit 80 may determine baseline cardiac signal features. During a confirmed normal sinus rhythm, for example, one or more of the R-wave amplitude, R-wave width, T-wave amplitude, P-wave amplitude, R-T time interval, R-P time interval, T-P time interval, and/or baseline noise may be determined. The R-T, R-P and T-P time intervals may be determined as time intervals between the absolute maximum peak amplitude of the respective R-, T- and P-waves or between other predefined fiducial points of these waves. The normal sinus rhythm may be confirmed manually or based on R-R intervals being greater than a tachyarrhythmia detection interval, no cardiac pacing being delivered, and/or an R-wave morphology match score greater than a predetermined threshold. The cardiac signal features may be determined by control circuit 80 from a digitized, filtered and rectified cardiac signal received from sensing circuit 86.

Alternatively, cardiac signal features may be determined manually from a cardiac electrical signal transmitted to and displayed by external device 40 or determined automatically by external device processor 52 from the transmitted cardiac electrical signal. The cardiac signal feature values may then be used by external device processor 52 for determining recommended R-wave sensing threshold control parameters, or the cardiac signal feature values may be programmed into ICD 14, stored in ICD memory 82, and retrieved by a processor included in control circuit 80 for use in determining R-wave sensing threshold control parameters.

With continued reference to the post-sense R-wave sensing threshold control parameters illustrated in FIG. 5, at block 606 of FIG. 11, a processor of control circuit 80 may determine control parameters for setting the starting value 116 of the R-wave sensing threshold. As described above in conjunction with FIG. 7, a variable gain applied to the sensitivity setting for determining a maximum R-wave sensing threshold limit may be determined based on the programmed sensitivity setting. The maximum R-wave sensing threshold limit is one control parameter used to determine the starting value 116. Another control parameter is the percentage of the maximum peak amplitude 112 of the currently sensed R-wave 104 that is used to determine the starting value 116. This percentage may be based on a T/R ratio of the peak T-wave voltage amplitude to the peak R-wave voltage amplitude 112 determined from the filtered, rectified cardiac electrical signal at block 604. For example, if the T/R ratio is 0.5, the starting R-wave sensing threshold may be determined as at least 0.6 or 0.7 of the maximum peak R-wave amplitude 112 or a percentage of at least 60% or 70%. If the T/R ratio is 0.3, the percentage may be set to 50% or some other percentage greater than the T/R ratio.

In other examples, a minimum limit of starting value 116 may be set based on the T-wave amplitude determined at block 604, e.g., a minimum limit of the starting value may be determined as a percentage greater than the maximum peak T-wave voltage amplitude, e.g., 125% of the peak T-wave voltage amplitude or 150% of the peak T-wave voltage amplitude, or a fixed interval greater than the peak T-wave voltage amplitude, e.g., 0.25 mV or 0.5 mV greater than the peak T-wave voltage amplitude.

At block 608, control circuit 80 may determine one or more control parameters for use in setting the second threshold value 118 (shown in FIG. 5). The second threshold value 118 may be set as a second percentage of the peak R-wave voltage amplitude 112 that is less than the percentage used to determine the starting value 116. This second percentage may be based on the P/R ratio of the maximum peak P-wave voltage amplitude to the maximum peak R-wave voltage amplitude 112 determined from the filtered, rectified cardiac electrical signal at block 604. For example, if the P/R ratio is 0.2, the second threshold value 118 may be determined as 0.4, or 40%, of the maximum peak R-wave amplitude. If the P/R ratio is 0.3, the percentage may be set to 50% or some other percentage greater than the P/R ratio.

In other examples, a minimum limit of the second threshold value 118 may be set based on the P-wave amplitude determined at block 604. For example, a minimum limit of the second threshold value 118 may be determined as a percentage of the P-wave amplitude, e.g., 125% of the P-wave amplitude or 150% of the P-wave amplitude, or a fixed amount greater than the maximum peak P-wave voltage amplitude, e.g., 0.2 mV or 0.3 mV, or other fixed amount than the peak P-wave amplitude.

At block 610, the control circuit 80 may set the second blanking interval 132 based on an R-wave width determined at block 604. As described previously, the first blanking interval 130 may be a hardware implemented blanking interval that is absolute and may define a minimum possible value of the second blanking interval 132. An R-wave width measurement may be determined at block 604 from a bandpass filtered cardiac electrical signal as the time interval from a fiducial point on the positive-going portion of the R-wave to a fiducial point on the negative-going portion of the R-wave, e.g., from the first positive crossing of a predetermined voltage to the last negative-going crossing of the predetermined voltage or from a maximum +dV/dt to a maximum −dV/dt. The second blanking interval 132 may be set to be at least equal to the determined R-wave width, a pre-determined portion of the R-wave width, or a fixed interval greater than or less than the R-wave width. The manner in which the second blanking interval 132 is determined based on an R-wave width may depend on how the R-wave width is determined. Example methods for determining an R-wave width are generally disclosed in U.S. Pat. No. 8,983,586 (Zhang) and U.S. Pat. No. 5,312,441 (Mader, et al.), both patents incorporated herein by reference in their entirety.

At block 612, control circuit 80 may determine the sense delay interval 134 based on the R-T interval determined at block 604. For example, sense delay interval 134 may be a fixed interval longer than the R-T interval, e.g., 20 ms longer than the measured R-T interval, or a predetermined percentage of the R-T interval, e.g., 120% of the R-T interval.

The drop time interval 136 may be determined by control circuit 80 at block 614 based on the R-P interval determined at block 604, e.g., as a fixed interval or percentage greater than the R-P interval. Since the R-T and R-P intervals may change with heart rate, the control circuit 80 may adjust the sense delay interval 134 and the drop time interval 136 based on heart rate (e.g., based on a most recent RR interval or a running average of a predetermined number of recent RR intervals) in addition to or alternatively to basing the values on the measured R-T and R-P intervals.

The programmed sensitivity setting may be determined and set at block 615 based on the P-wave amplitude and/or baseline noise determined at block 604. A baseline noise amplitude may be determined by measuring the peak cardiac signal amplitude during a baseline window set between cardiac events, e.g., after the T-wave and before an R-wave. The sensitivity setting may be determined as the lowest setting that is greater than the determined baseline noise amplitude or a fixed interval or percentage greater than the determined baseline noise amplitude.

At block 616, control circuit 80 may be configured to compare the R-wave sensing threshold control parameters to the population-based VT/VF detection sensitivity data stored at block 602. The R-wave sensing threshold control parameters may include a combination of automatically determined control parameters set by control circuit 80 as described above and/or user-programmed control parameters. Individual control parameter settings or combinations of control parameter settings may be compared to VT/VF detection sensitivity data to predict the expected sensitivity for detecting VT and VF when the currently selected R-wave sensing threshold control parameters are utilized.

If any of the control parameters, individually or in combination, result in an expected VT/VF detection sensitivity that is less than the alert threshold (e.g., threshold 658 in FIG. 12), an alert condition is detected at block 618. In response to detecting an alert condition, control circuit 80 may generate an alert notification at block 620 that is transmitted to external device 40 and displayed on user display 54. A user may then review the programmed settings and make any adjustments needed to improve the expected VT/VF detection sensitivity or accept the programmed settings without adjustments. The programmed settings with any adjustments may be transmitted back to ICD 14 and stored in memory 82 at block 622 for use in controlling the R-wave sensing threshold.

In some examples, detection sensitivity data are stored in memory 82 of ICD 14 and the process of flow chart 600 is performed automatically by control circuit 80 for setting the sensing threshold control parameters. A targeted VT/VF detection sensitivity value may be programmed into ICD 14 by a user and ICD 14 may determine the sensing threshold control parameters based on the targeted sensitivity and the baseline cardiac signal features. This process may be repeated periodically for updating the sensing threshold control parameters.

In other examples, the VT/VF detection sensitivity data stored at block 602 is stored in memory 53 of external device 40. The operations of blocks 604 through 618 may be performed by a processor included in control circuit 80, by external device processor 52 after receiving a cardiac electrical signal episode from ICD 14 via ICD telemetry circuit 88 and external device telemetry unit 58, or cooperatively by a processor of control circuit 80 and external device processor 52 with some steps or operations performed by control circuit 80 and some performed by processor 52. Processor 52 may perform the comparison at block 616 and generate the display of the alert notification at block 620 on display 54 in response to detecting an alert condition at block 618. Upon user acceptance of the programmed settings of the R-wave sensing threshold control parameters, after any adjustments made based on an alert if generated, external device 40 transmits the programmable control parameter settings to ICD 14.

Figure 14:
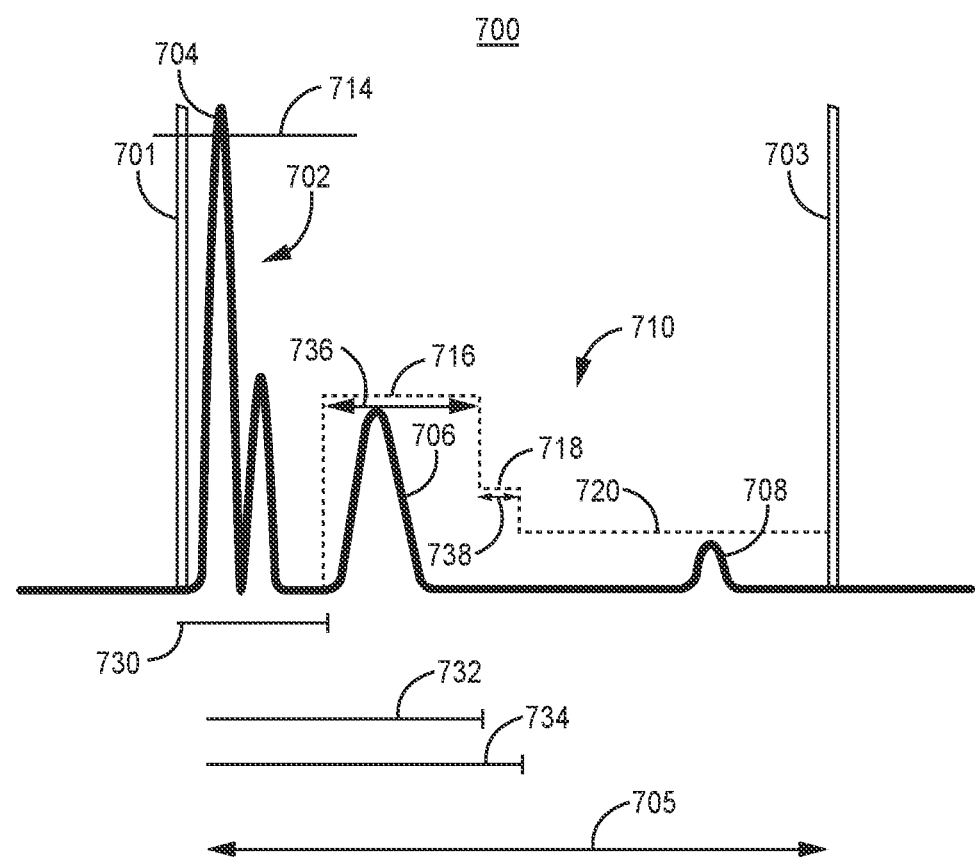
FIG. 14 is a timing diagram showing ventricular pacing pulses and a band-passed filtered and rectified cardiac electrical signal and the R-wave sensing threshold.

FIG. 14 is a timing diagram 700 showing ventricular pacing pulses 701 and 703 and a band-passed filtered and rectified cardiac electrical signal 702. The cardiac electrical signal 702 includes a pacing-evoked R-wave 704 followed by T-wave 706 and P-wave 708. During atrio-ventricular block, P-wave 708 may not be conducted to the ventricles such that a pacing interval 705 expires. Pacing pulse 703 is delivered at the pacing interval 705 following the preceding pulse 701 if pacing interval expires without cardiac electrical signal 702 crossing the R-wave sensing threshold 710. The pacing interval 705 may be a lower rate interval for bradycardia pacing, a back-up pacing interval to prevent asystole during post-shock pacing, an anti-tachycardia pacing pulse, or other pacing interval set according to a programmed pacing therapy protocol.

The post-pulse R-wave sensing threshold 710 is controlled by control circuit 80 and sensing circuit 86. Upon delivery of ventricular pacing pulse 701, a post-pulse blanking interval 730 is started. The post-pulse blanking interval may be a fixed time interval controlled by hardware that prevents sensing the pacing-evoked R-wave 704 and any post-pace polarization artifact. The post-pulse blanking interval 730 may be 250 ms in one example, and may be 200 ms to 500 ms in other examples. The post-pulse blanking interval 730 may be longer than the post-sense blanking intervals 130 and 132 (FIG. 5). The example of post-pulse R-wave sensing threshold 710 shown in FIG. 14 generally relates to a pacing pulse, however the post-pulse control parameters used for controlling the post-pulse R-wave sensing threshold 710 may be used or adjusted for use following a CV/DF shock or other electrical stimulation pulses, such as an electrical stimulation pulse delivered for VT or VF induction as described in conjunction with FIG. 10. For instance, an even longer post-pulse blanking interval, e.g., up to 2 seconds, may be used following a CV/DF shock pulse to allow longer post-stimulation polarization recovery.

At the expiration of the post-pulse blanking interval 730, the R-wave sensing threshold 710 is set to a post-pulse starting threshold value 716, which may be based directly on the programmed sensitivity setting or on a maximum threshold limit 714. The maximum threshold limit 714 may be established by using a sensitivity-dependent gain as described above. For instance, the gain applied to a programmed sensitivity may be computed as 8+1.8/S where S is the programmed sensitivity. To obtain the maximum threshold limit 714, this gain is multiplied by the sensitivity S resulting in the maximum threshold limit 714 being set to eight times the programmed sensitivity setting plus 1.8. This maximum threshold limit 714 may be the same as the maximum threshold limit 114 (FIG. 5) established for use in controlling the starting R-wave sensing threshold value following a sensed intrinsic R-wave. During pacing, the maximum peak amplitude of an evoked R-wave 704 may not be determined for setting the starting value 716 of R-wave sensing threshold 710. The pacing-evoked R-wave signal amplitude may not be predictive of the amplitude of intrinsic R-waves. The maximum threshold limit 714 may therefore be used for determining the post-pulse starting and second threshold values 716 and 718 of the R-wave sensing threshold 710 following pacing pulse 701 without determining a peak amplitude of pacing-evoked R-wave 704.

The starting threshold value 716 may be a first percentage of the maximum threshold limit 714, and the second threshold value 718 may be a second percentage of the maximum threshold limit 714. In an illustrative example, the starting threshold value 716 may be approximately 31% of the maximum threshold limit 714, and the second threshold value 718 may be approximately 15% of the maximum threshold value 714. The percentages used to set the starting and second threshold values 716 and 718 may be programmable and may range from 10 to 50% or higher (with the second percentage being less than the first percentage).

The starting threshold value 716 is held during post-pulse delay interval 732, from the expiration of the post-pace blanking interval 730 until expiration of the delay interval 732. Delay interval 732 may be a fixed, programmable time interval, e.g., 500 ms to encompass the T-wave 706, or at least the peak of the T-wave or a majority of the T-wave 706, to avoid T-wave oversensing. The post-pulse delay interval 732 may be optimized to minimize the likelihood of T-wave oversensing as generally described previously in conjunction with FIG. 5 with regard to sense delay interval 134. Delay interval 732 may be dependent on the post-pulse blanking period 730, e.g., 250 ms longer than the post-pulse blanking period but not greater than a drop time interval 734 as described below.

Upon expiration of the delay interval 732, the sensing circuit 86 adjusts R-wave sensing threshold 710 from the starting value 716 to the second threshold value 718, lower than the starting value 716. R-wave sensing threshold 710 is held at the intermediate threshold value 718 until the expiration of drop time interval 734. Drop time interval 734 may be started upon delivery of pacing pulse 701. Drop time interval 734 may be determined by control circuit 80 based on a paced heart rate, e.g., based on the pacing interval 705. In one example, drop time interval 734 is set to 50% of the pacing interval 705 but may be set to other percentages, greater or less than 50%, of the pacing interval 705.

In some examples, the drop time interval 734 may be set within a limited range, e.g., up to a maximum upper limit and/or down to a minimum lower limit. For example, the maximum drop time interval may be 600 to 750 ms following an electrical stimulation pulse. The drop time interval 734 may have a minimum lower limit so that the drop time interval 734 does not expire earlier than the delay interval 732.

The drop time interval 734 determined as a selected percentage of the pacing interval 705 may be compared to a minimum drop time interval, which may be equal to delay interval 732. If the drop time interval 734 determined as a percentage of the pacing interval 705 is equal to or less than the minimum drop time interval, sensing circuit 86 may set the drop time interval equal to the minimum drop time interval. When the minimum drop time interval equals the delay interval 732, the R-wave sensing threshold 710 may be held at the starting threshold value 716 for the portion 736 of the delay interval 732 extending from the expiration of blanking period 730 to the expiration of delay interval 732. Upon expiration of delay interval 732, the R-wave sensing threshold 710 is adjusted to the minimum sensing threshold 720.

In response to the drop time interval determined as a percentage of the pacing interval 705 being equal to or less than the delay interval 732, the drop time interval may be set equal to the delay interval 732 such that the cardiac event sensing threshold is held at a first threshold value equal to the starting threshold value 716 from the expiration of the post-pulse blanking period 730 until expiration of the drop time interval. The intermediate sensing threshold 718 determined as a second percentage of the maximum threshold limit 714 may be skipped. The drop time interval 734 and the delay interval 732 may expire simultaneously such that the starting sensing threshold value 716 is adjusted to the minimum sensing threshold 720 without R-wave sensing threshold 710 being set to the intermediate sensing threshold value 718 before dropping to the minimum sensing threshold value 720.

In another example, if the drop time interval 734 determined as a percentage of the pacing interval 705 is shorter than the sense delay interval 732, the sense delay interval 732 may be truncated to be equal to the drop time interval 734. Upon expiration of the post-pulse blanking interval, the R-wave sensing threshold 710 is set equal to the starting value 716 and held at that value until the simultaneous expiration of the drop time interval 734 and the sense delay interval 732. The R-wave sensing threshold 710 may be adjusted from the starting value 716 to the minimum sensing threshold value 720 upon expiration of the drop time interval 734 and truncated sense delay interval 732. The intermediate threshold value 718 may be skipped.

The pacing interval 705 may be set to various time intervals depending on the electrical stimulation therapy that is being delivered. As such, the drop time interval 734 may be determined as a percentage of the pacing interval 705 associated with the electrical stimulation therapy that is being delivered in accordance with a determined need for the therapy. Different minimum drop time intervals may be set for different electrical stimulation therapies. For example, the delay interval 732, which may be set as a fixed interval longer than the post-pulse blanking interval 730, may be longer following a CV/DF shock or post-shock pacing pulse than the delay interval following a bradycardia pacing pulse. If the minimum drop time interval is set to be equal to the delay interval 732, the minimum drop time interval that may be set for controlling the R-wave sensing threshold following a CV/DF shock and/or a post-shock pacing pulse may be longer than the minimum drop time interval that may be set for controlling the R-wave sensing threshold following a bradycardia pacing pulse. For example, the minimum drop time interval post-shock and/or during post-shock pacing may be 800 ms, and the minimum drop time interval following a bradycardia pacing pulse, e.g., during VVI pacing, may be 500 ms. These minimum drop time intervals may equal corresponding delay intervals used during the respective electrical stimulation therapy. A maximum drop time interval may be set as a fixed value, e.g., up to 800 ms or more, and in some examples different fixed maximum drop time intervals may be stored in memory 82 to be used following different types of electrical stimulation pulses (e.g., following a shock pulse, a post-shock pacing pulse, a VVI pacing pulse, etc.)

When the drop time interval 734 determined as a percentage of the pacing interval 705 exceeds the delay interval 732, the R-wave sensing threshold 710 is adjusted from the starting sensing threshold value 716 to the intermediate sensing threshold value 718. R-wave sensing threshold 710 may be held at the second sensing threshold value 718 for the portion 738 of drop time interval 734 after expiration of sense delay interval 732. Upon expiration of the drop time interval 734, the R-wave sensing threshold 710 is adjusted to the minimum sensing threshold value 720, or the "sensing floor," if the cardiac electrical signal 702 has not yet crossed the R-wave sensing threshold 710. The minimum sensing threshold value 720 may be set equal to the programmed sensitivity setting as described above, which may be, for example, 0.075 mV, 0.15 mV, 0.3 mV, 0.6 mV or higher. The R-wave sensing threshold 710 remains at the minimum sensing threshold 720 until the cardiac electrical signal 702 crosses the threshold 710 or pacing interval 705 expires, whichever occurs first. In the example shown, pacing interval 705 expires, and pacing pulse 703 is delivered.

Figure 15:
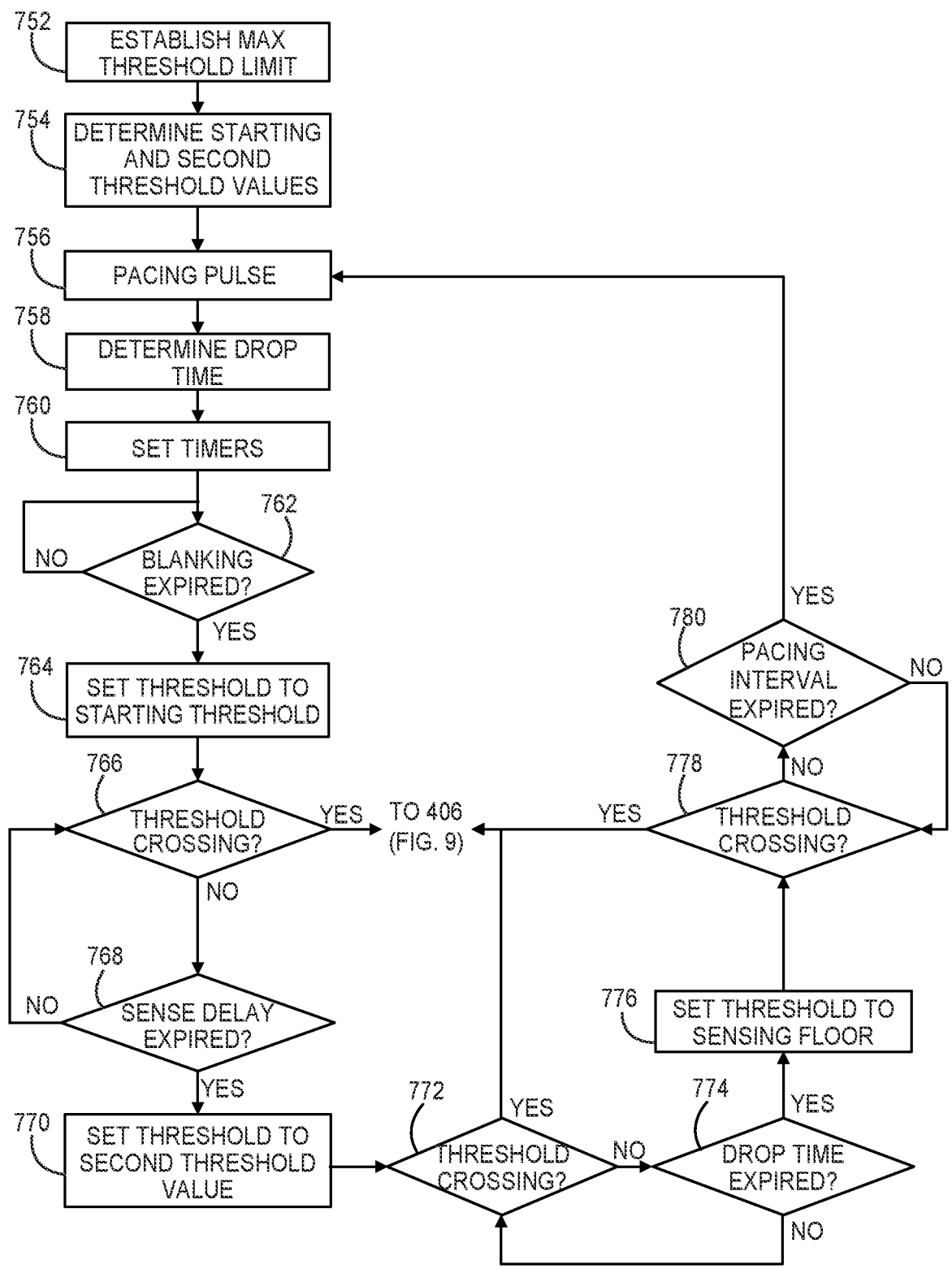
FIG. 15 is a flow chart of a method for controlling the R-wave sensing threshold following an electrical stimulation pulse.

FIG. 15 is a flow chart 750 of a method for controlling the R-wave sensing threshold following an electrical stimulation pulse. The methods described in conjunction with flow chart 750 generally relate to controlling the R-wave sensing threshold following a pacing pulse, however, the R-wave sensing threshold may be controlled in the same or similar manner following other electrical stimulation pulses, such as a CV/DF shock pulse or a T-wave shock for inducing ventricular tachyarrhythmia.

At block 752, control circuit 80 establishes a maximum threshold limit. As described above, the maximum threshold limit may be set by determining a multiple of the programed sensitivity setting and/or adding a predetermined constant. In one example, the maximum threshold limit is set to eight times the programmed sensitivity setting plus 1.8. The maximum threshold limit determined at block 752 may be the same maximum threshold limit determined at block 402 of FIG. 9 for establishing a maximum R-wave sensing threshold value that may be set following a sensed intrinsic R-wave. In some cases, the maximum threshold limit may be determined using a sensitivity-dependent gain. In other examples, the maximum threshold limit determined at block 752 may be determined differently than the maximum threshold limit determined at block 402 of FIG. 9.

The maximum R-wave sensing threshold limit determined at block 752 is used at block 754 to determine the starting and second, intermediate sensing threshold values based on the programmed sensitivity setting. The maximum R-wave sensing threshold determined at block 402 of FIG. 9 sets a maximum limit of the starting R-wave sensing threshold value determined based on the peak amplitude determined during a post-sense blanking interval as described in conjunction with FIGS. 5 and 9 above.

Since the starting and second, intermediate threshold values used after an electrical stimulation pulse are not based on determined a peak amplitude of an R-wave, these values may be pre-determined, prior to a delivered pacing pulse. The starting and second threshold values used following a pacing pulse, therefore, do not need to be determined on a beat-by-beat basis during a blanking interval. The starting and second threshold values used following an intrinsic, sensed R-wave may be determined beat-by-beat since they are based on the peak R-wave amplitude determined during the post-sense blanking interval. The post-pulse starting and second threshold values used following an electrical stimulation pulse may be determined a single time for a given programmed sensitivity setting and may be re-determined only in response to a change in the programmed sensitivity setting.

The starting threshold value determined at block 754 may be a first percentage of the maximum threshold limit, and the second, intermediate threshold value may be a second percentage of the maximum threshold limit. As described above, the starting threshold value may be 31% of the maximum threshold limit and the intermediate threshold value may be 15% of the maximum threshold limit though other percentages or relative ratios of the maximum threshold limit (or programmed sensitivity setting) may be used.

A pacing pulse may be delivered at block 756 according to a programmed pacing protocol. The pacing pulse is delivered at a pacing interval following a preceding pacing pulse or sensed intrinsic R-wave. The pacing interval may be a lower rate interval set to control bradycardia pacing (e.g., VVI pacing) a post-shock back-up pacing rate interval, an ATP interval or other time interval used to control the delivery of an electrical stimulation pulse by therapy delivery circuit 84.

Control circuit 80 determines the drop time interval at block 758 based on the pacing interval. The drop time interval may be set to a percentage of the pacing interval, e.g., one-half of the pacing interval. As described above, the drop time interval may be set to a predetermined percentage of the pacing interval but not less than a predetermined minimum interval. In some examples, the drop time interval may not be set less than the delay interval 732 shown in FIG. 14. In other examples, if the drop time interval determined at block 758 is shorter than the sense delay interval, the sense delay interval is truncated to be equal to the drop time interval.

The drop time interval may be set to the predetermined percentage of the pacing interval but not more than a maximum drop time, which may be a fixed time interval, e.g., 600 to 750 ms. While the drop time is shown to be determined at block 758 after pacing pulse delivery, it is recognized that the drop time interval may be determined prior to pacing pulse delivery, while the pacing interval is running, in anticipation of a delivered pacing pulse and post-pulse R-wave sensing.

At block 760, control circuit 80 sets timers or counters for controlling the multi-level R-wave sensing threshold following the pacing pulse. For example, the post-pulse blanking interval, which may be a digital blanking interval controlled by firmware stored in memory 82, the sense delay interval, the determined drop time interval and a pacing interval may each be started upon delivery of the pacing pulse at block 756. The post-pulse blanking interval may be longer than the blanking interval used after a sensed R-wave. The post-pulse blanking interval may be a digital blanking interval that is 250 ms long following a pacing pulse. The post-pulse blanking interval may be longer, e.g., 800 ms or longer, when the delivered electrical stimulation pulse is a CV/DF shock pulse. The post-pulse blanking interval may be programmable and set between 250 ms following a pacing pulse and up to 2 seconds following a shock pulse.

Upon expiration of the post-pulse blanking interval, as determined at block 762, the sensing circuit 86 sets the starting R-wave sensing threshold at block 764 to the starting threshold value determined at block 754. If the cardiac electrical signal crosses the starting R-wave sensing threshold, as determined at block 766, the process returns to block 406 of FIG. 9 where sensing circuit 86 produces an R-wave sensed event signal and restarts the various control time intervals for controlling the R-wave sensing threshold following a sensed R-wave as described above in conjunction with FIG. 9.

If the sense delay interval expires at block 768 before the cardiac electrical signal crosses the R-wave sensing threshold, sensing circuit 86 adjusts the R-wave sensing threshold at block 770 to the second threshold value determined at block 754. If the cardiac electrical signal received by sensing circuit 86 crosses the R-wave sensing threshold adjusted to the second threshold value, as determined at block 772, the process advances to block 406 of FIG. 9 to generate an R-wave sensed event signal and reset the post-sense R-wave sensing threshold control time intervals as described above. In the case of the drop time interval being set equal to the delay interval, such that both expire at block 768, adjustment from the starting threshold to the second, intermediate threshold value at block 770 may be skipped and the process advances to block 774.

If the drop time interval expires at block 774 without the cardiac electrical signal crossing the R-wave sensing threshold (block 772), the sensing circuit 86 adjusts the R-wave sensing threshold to the minimum threshold value or sensing floor, which may be the programmed sensitivity setting, at block 776. In other examples, more than two drop steps in the sensing threshold value may be implemented and adjusted at the expiration of respective drop time intervals, e.g., each set to different percentages of the pacing interval.

Sensing circuit 86 waits for the cardiac electrical signal to cross the sensing floor at block 778 and for the pacing interval to expire at block 780, whichever occurs first. If the cardiac electrical signal crosses the minimum sensing threshold at block 778, the process advances to block 406 of FIG. 9 to generate an R-wave sensed event signal and control the R-wave sensing threshold using the post-sense R-wave sensing threshold control parameters. If the pacing interval expires without an R-wave sensing threshold crossing as determined at block 780, a pacing pulse is delivered at block 756. The process of flow chart 750 continues controlling the R-wave sensing threshold using the post-pace R-wave sensing threshold control parameters following the pacing pulse. The drop time may be re-determined at block 758 if the pacing interval has changed so that the drop time interval is adjusted dynamically with changes in pacing rate. The pacing interval may change as a result of user programming, rate-responsive pacing based on patient activity, an ATP protocol that uses different inter-pulse intervals, or a change in the electrical stimulation therapy being delivered.

Figure 16:
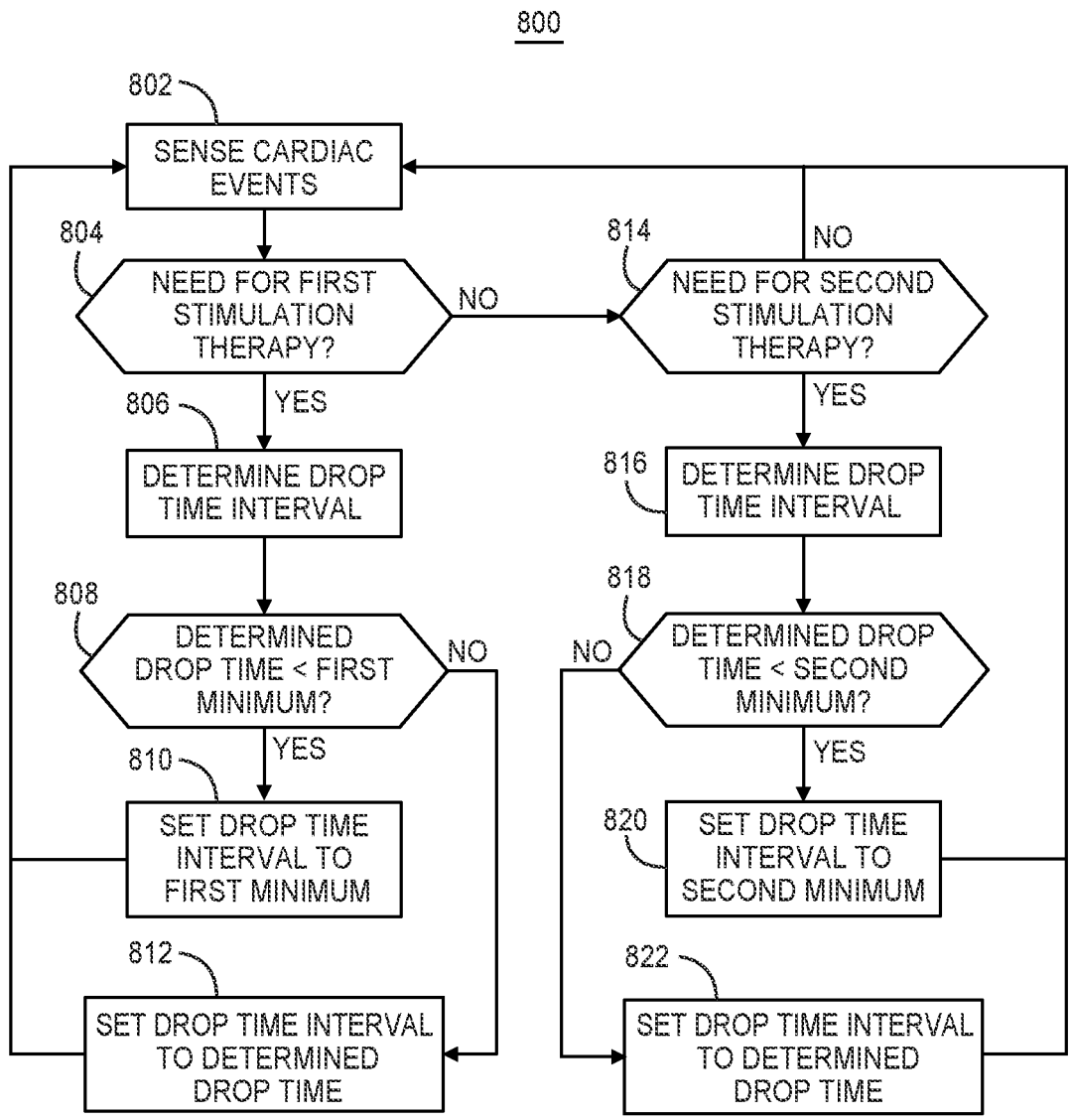
FIG. 16 is a flow chart of a method for controlling the R-wave sensing threshold by an implantable medical device according to another example.

FIG. 16 is a flow chart 800 of a method for controlling the R-wave sensing threshold by an implantable medical device according to another example. At block 802, sensing circuit 86 of ICD 14 may sense cardiac events in a cardiac electrical signal based on cardiac event sensing threshold crossings by the received cardiac signal. Prior to detecting a need for an electrical stimulation therapy, control circuit 80 may control the cardiac event sensing threshold used by sensing circuit 86 at block 802 according the techniques for controlling the post-sense R-wave sensing threshold as described in conjunction with any of FIGS. 5-9.

ICD 14 may be configured to determine a need for a first electrical stimulation therapy at block 804 based on a rate of the sensed cardiac events, which may be a predetermined number of most recent sensed cardiac events. For example, ICD 14 may detect a tachyarrhythmia based on a required number of cardiac event intervals determined between consecutively sensed cardiac events, e.g., R-waves, falling into a tachyarrhythmia detection interval zone. The rate of the cardiac events may therefore lead to a tachyarrhythmia detection resulting in control circuit 80 determining a need for ATP and/or a CV/DF shock. In another example, the rate of sensed cardiac events may lead to control circuit 80 determining a need for a CV/DF shock and post-shock pacing in the case of a sensed cardiac event not occurring during a post-shock pacing interval following the CV/DF shock.

If a need for a first electrical stimulation therapy is determined, control circuit 80 determines the drop time interval at block 806 for use following an electrical stimulation pulse delivered according to the first stimulation therapy. The drop time interval may be determined at block 806 as a percentage of a pacing interval of the first stimulation therapy, e.g., as a percentage of a post-shock pacing interval when a need for a CV/DF shock is determined or as a percentage of an ATP interval when a need for ATP is determined.

The determined drop time interval may be compared to a first minimum drop time interval corresponding to the first stimulation therapy. The percentage of the pacing interval used to determine the drop time interval at block 806 may be a programmable value. The sense delay interval set in response to a delivered electrical stimulation pulse during the first stimulation therapy may be a fixed or programmable value. In some instances the drop time interval determined at block 806 as a percentage of a pacing interval of the first stimulation therapy may be less than the sense delay interval. The first minimum drop time interval may be equal to the sense delay interval used to control the cardiac event sensing threshold during the first stimulation therapy in some examples. In other examples, the first minimum drop time interval compared to the determined drop time interval at block 808 may be greater or less than the sense delay interval associated with the first stimulation therapy.

At block 810, control circuit 80 sets the drop time interval to the greatest one of the first minimum drop time interval and the determined drop time interval. The process returns to block 802 to sense cardiac events according to the post-pulse cardiac event sensing threshold control parameters during the first stimulation therapy, until an intrinsic cardiac event is sensed. If the minimum drop time interval is set equal to or less than the sense delay interval at block 810, the control circuit 80 may control the sensing circuit 86 to hold the cardiac event sensing threshold at a first threshold value set equal to the starting threshold value determined based on the maximum threshold limit for the portion of the drop time interval extending from the expiration of the post-pulse blanking period until the expiration of the drop time interval. If the minimum drop time interval is greater than the sense delay interval, the control circuit 80 may control sensing circuit 86 to hold the cardiac event sensing threshold at a starting threshold value set to a first percentage of the maximum threshold limit until the expiration of the sense delay interval and hold the sensing threshold at a next, lower threshold value set to a second percentage of the maximum threshold limit from the expiration of the delay interval until the expiration of the drop time interval.

If the determined drop time interval is greater than the first minimum drop time interval associated with the first stimulation therapy, "no" branch of block 808, control circuit 80 sets the drop time interval to the determined drop time interval at block 812 and returns to block 802 to control the cardiac event sensing threshold according to the post-pulse cardiac event sensing threshold control parameters corresponding to the first stimulation therapy. The sensing circuit 86 is configured to hold the cardiac event sensing threshold at a predetermined percentage of the maximum threshold limit during the drop time interval. The cardiac event sensing threshold is held at the predetermined percentage of the maximum threshold for the portion of the drop time interval extending from the expiration of the sense delay interval until expiration of the drop time interval in some examples. The cardiac event sensing threshold may be set to a starting threshold value set as a first percentage of the maximum threshold limit during a delay interval and be held at the second threshold set to a second, lower percentage of the maximum threshold limit during the drop time interval. In this way, the cardiac event sensing threshold is equal to or greater than second threshold value from the expiration of the post-pulse blanking period until expiration of the drop time interval.

In some examples, control circuit 80 is configured to determine a need for a second electrical stimulation therapy. If a need for the first stimulation therapy is not detected, "no" branch of block 84, control circuit 80 may determine a need for the second electrical stimulation therapy at block 814. The need for the second electrical stimulation therapy may also be based on a rate of sensed cardiac events. For example, if a cardiac event is not sensed during a pacing interval such that the rate of sensed cardiac events is less than a programmed pacing rate, control circuit 80 determines a need for the second electrical stimulation therapy, e.g., a ventricular pacing pulse.

Determining a need for an electrical stimulation therapy at block 804 or 814 may be performed by control circuit 80 according to any implemented arrhythmia detection algorithm or as generally disclosed in any of the incorporated references. If control circuit 80 does not determine a need for an electrical stimulation therapy at either of blocks 804 or 814, sensing circuit 86 continues to sense cardiac events at block 802 based on an R-wave sensing threshold controlled according to the post-sense control parameters as described herein, e.g., in conjunction with any of FIGS. 5-9.

Control circuit 80 is configured to respond to determining the need for the second electrical stimulation therapy by determining a drop time interval at block 816 based on a pacing interval of the second electrical stimulation therapy. The drop time interval determined as a percentage of the pacing interval of the second electrical stimulation therapy is compared to a second minimum drop time interval at block 818. The second minimum drop time interval may be different than the first minimum drop time interval. For example, the sense delay interval used following an electrical stimulation pulse may be set to a post-pulse blanking interval plus a predetermined time interval, e.g., 250 ms. The post-pulse blanking interval may be longer during the first stimulation therapy, e.g., up to 800 ms, up to 1,500 ms or even up to two seconds, compared to the post-pulse blanking interval used during the second stimulation therapy, e.g., up to 250 ms. The post-pulse sense delay interval during the first stimulation therapy may be 1000 ms or more, for example and the post-pulse sense interval during the second stimulation therapy may be 500 ms, for example. The first minimum drop time interval may be set to the first sense delay interval, and the second minimum drop time interval may be set to the second sense delay interval, which may be shorter than the first delay interval.

The control circuit 80 is configured to set the drop time interval to the greatest one of the second minimum drop time interval (at block 820) and the drop time interval determined as a percentage of a pacing interval of the second stimulation therapy (at block 822). The process returns to block 802 to control the cardiac event sensing threshold according to the set drop time interval and other post-pulse cardiac event sensing threshold control parameters associated with the second stimulation therapy.

For example, control circuit 80 controls sensing circuit 86 to hold the R-wave sensing threshold at a threshold value determined as a percentage of the maximum threshold limit during the set drop time interval. As described above, the sensing circuit 86 may set the R-wave sensing threshold to a starting threshold value set as a first percentage of the maximum threshold limit after expiration of a post-pulse blanking interval, adjust the R-wave sensing threshold to a second threshold value determined as a second percentage of the maximum threshold limit upon expiration of the sense delay interval, hold the R-wave sensing threshold at the second threshold value until the expiration of the set drop time interval, and adjust the R-wave sensing threshold to a minimum sensing threshold value upon expiration of the set drop time interval, as long as the cardiac electrical signal does not cross the R-wave sensing threshold. If an intrinsic cardiac event is sensed at block 802, control circuit 80 and sensing circuit 86 return to controlling the cardiac event sensing threshold according to post-sense control parameters.

In this way, control of the cardiac event sensing threshold may alternate between post-sense control parameters and post-pulse control parameters corresponding to one or more electrical stimulation therapies. In each of these situations, the drop time interval used to control adjustment from a threshold value to the minimum sensing threshold may be dynamically determined based on a heart rate, which may be a sensed intrinsic rate or a paced rate. When the drop time interval is based on a paced rate after determining a need for an electrical stimulation therapy, the drop time interval may be determined based on a pacing interval of an electrical stimulation therapy pulse that is scheduled or has been delivered. In other instances, the control of the cardiac event sensing threshold may alternate between post-sense control parameters which have fixed drop times and post-pulse control parameters corresponding to one or more electrical stimulation therapies that utilize dynamic drop times based on pacing interval or other heart rate intervals.

Thus, a method and apparatus for controlling a cardiac event sensing threshold by an IMD system have been presented in the foregoing description with reference to specific embodiments. In other examples, various methods described herein may include steps performed in a different order or combination than the illustrative examples shown and described herein. It is appreciated that various modifications to the referenced embodiments may be made without departing from the scope of the disclosure and the following claims.

The invention claimed is:

1. A medical device comprising:
a therapy delivery circuit configured to deliver an electrical stimulation pulse to a patient's heart;
a control circuit configured to:
schedule a next electrical stimulation pulse to be delivered by the therapy delivery circuit at a pacing interval; and
determine a drop time interval based on the pacing interval; and
a sensing circuit configured to:
receive a cardiac electrical signal;
apply a cardiac event sensing threshold to the cardiac electrical signal by holding the cardiac event sensing threshold at a first threshold value starting after the electrical stimulation pulse until an expiration of the drop time interval determined based on the pacing interval; and
sense a cardiac event attendant to a myocardial depolarization of the patient's heart in response to the cardiac electrical signal crossing the cardiac event sensing threshold.

2. The medical device of claim 1, wherein the sensing circuit is further configured to adjust the cardiac event sensing threshold from the first threshold value to a minimum sensing threshold value upon expiration of the drop time interval.

3. The medical device of claim 1, wherein:
the therapy delivery circuit is configured to deliver the electrical stimulation pulse as a cardioversion/defibrillation shock; and the control circuit is configured to schedule the next electrical stimulation pulse as a post-shock pacing pulse at the pacing interval set to a post-shock pacing interval.

4. The medical device of claim 1, wherein:
the therapy delivery circuit is configured to deliver the electrical stimulation pulse as a cardiac pacing pulse; and
the control circuit is configured to schedule the next electrical stimulation pulse as a next cardiac pacing pulse at the pacing interval set to one of an anti-tachycardia pacing interval or a lower rate interval for bradycardia pacing.

5. The medical device of claim 1, wherein the control circuit is further configured to:
establish a maximum threshold limit based on a minimum sensing threshold value equal to a programmed sensitivity setting; and
determine the first threshold value based on the maximum threshold limit.

6. The medical device of claim 5, wherein:
the control circuit is further configured to determine a starting threshold value of the cardiac event sensing threshold based the maximum threshold limit, the starting threshold value being a greater percentage of the maximum threshold limit than the first threshold value; and
the sensing circuit is further configured to apply the cardiac event sensing threshold to the cardiac electrical signal by:
starting a post-pulse blanking interval and a post-pulse delay interval upon delivery of the electrical stimulation pulse by the therapy delivery circuit;
holding the cardiac event sensing threshold at the starting threshold value from an expiration of the post-pulse blanking interval until an expiration of a post-pulse delay interval; and
upon expiration of the post-pulse delay interval, adjusting the cardiac event sensing threshold from the staring threshold value to the first threshold value.

7. The medical device of claim 5, wherein the control circuit is further configured to establish the maximum threshold limit based on the minimum sensing threshold value by:
determining a gain based on the programmed sensitivity setting, the gain being inversely related to the programmed sensitivity setting; and
determining the maximum threshold limit as the product of the gain and the programmed sensitivity setting.

8. The medical device of claim 1, wherein:
the control circuit is further configured to detect an expiration of the pacing interval without the cardiac electrical signal crossing the applied cardiac event sensing threshold; and
the therapy delivery circuit is configured to deliver the next electrical stimulation pulse upon the expiration of the pacing interval.

9. The medical device of claim 1, wherein:
the control circuit is further configured to:
determine, based on the cardiac electrical signal received by the sensing circuit, a need for one of a first electrical stimulation therapy or a second cardiac electrical stimulation therapy different than the first electrical stimulation therapy;
in response to determining the need for the first electrical stimulation therapy:
compare the drop time interval determined based on the pacing interval to a first minimum drop time interval; and
set the drop time interval used by the sensing circuit to a greatest one of the drop time interval determined based on the pacing interval and the first minimum drop time interval; and
in response to determining the need for the second electrical stimulation therapy:
compare the drop time interval determined based on the pacing interval to a second minimum drop time interval that is different than the first minimum drop time interval; and
set the drop time interval to a greatest one of the drop time interval determined based on the pacing interval and the second minimum drop time interval.

10. The medical device of claim 1, further comprising a housing enclosing the therapy delivery circuit, the control circuit and the sensing circuit, the housing configured to receive a lead carrying at least one electrode; and
the sensing circuit is configured to receive the cardiac electrical signal and sense the cardiac event when the at least one electrode is not in contact with myocardial tissue.

11. A method comprising:
delivering an electrical stimulation pulse to a patient's heart;
scheduling a next electrical stimulation pulse to be delivered at a pacing interval;
determining a drop time interval based on the pacing interval;
receiving a cardiac electrical signal by sensing circuitry of a medical device;
applying by the sensing circuitry a cardiac event sensing threshold to the cardiac electrical signal by holding the cardiac event sensing threshold at a first threshold value starting after the electrical stimulation pulse until an expiration of the drop time interval determined based on the pacing interval; and
sensing a cardiac event attendant to a myocardial depolarization of the patient's heart in response to the cardiac electrical signal crossing the cardiac event sensing threshold.

12. The method of claim 11, further comprising adjusting the cardiac event sensing threshold from the first threshold value to a minimum sensing threshold value upon expiration of the drop time interval.

13. The method of claim 11, further comprising:
delivering the electrical stimulation pulse as a cardioversion/defibrillation shock; and
scheduling the next electrical stimulation pulse as a post-shock pacing pulse at the pacing interval set to a post-shock pacing interval.

14. The method of claim 11, further comprising:
delivering the electrical stimulation pulse as a cardiac pacing pulse; and
scheduling the next electrical stimulation pulse as a next cardiac pacing pulse at the pacing interval set to one of an anti-tachycardia pacing interval or a lower rate interval for bradycardia pacing.

15. The method of claim 11, further comprising:
establish a maximum threshold limit based on a minimum sensing threshold value equal to a programmed sensitivity setting; and
determine the first threshold value based on the maximum threshold limit.

16. The method of claim 15, further comprising:
determining a starting threshold value of the cardiac event sensing threshold based the maximum threshold limit, the starting threshold value being a greater percentage of the maximum threshold limit than the first threshold value; and
applying the cardiac event sensing threshold to the cardiac electrical signal by:
- starting a post-pulse blanking interval and a post-pulse delay interval upon delivery of the electrical stimulation pulse;
- holding the cardiac event sensing threshold at the starting threshold value from an expiration of the post-pulse blanking interval until an expiration of a post-pulse delay interval; and
- upon expiration of the post-pulse delay interval, adjusting the cardiac event sensing threshold from the staring threshold value to the first threshold value.

17. The method of claim 15, wherein the control circuit is further configured to establish the maximum threshold limit based on the minimum sensing threshold value by:
- determining a gain based on the programmed sensitivity setting, the gain being inversely related to the programmed sensitivity setting; and
- determining the maximum threshold limit as the product of the gain and the programmed sensitivity setting.

18. The method of claim 11, further comprising:
- detecting an expiration of the pacing interval without the cardiac electrical signal crossing the applied cardiac event sensing threshold; and
- delivering the next electrical stimulation pulse upon the expiration of the pacing interval.

19. The method of claim 11, further comprising:
- determining, based on the cardiac electrical signal received by the sensing circuit, a need for one of a first electrical stimulation therapy or a second cardiac electrical stimulation therapy different than the first electrical stimulation therapy;
- in response to determining the need for the first electrical stimulation therapy:
  - comparing the drop time interval determined based on the pacing interval to a first minimum drop time interval; and
  - setting the drop time interval used by the sensing circuit to a greatest one of the drop time interval determined based on the pacing interval and the first minimum drop time interval; and
- in response to determining the need for the second electrical stimulation therapy:
  - comparing the drop time interval determined based on the pacing interval to a second minimum drop time interval that is different than the first minimum drop time interval; and
  - setting the drop time interval to a greatest one of the drop time interval determined based on the pacing interval and the second minimum drop time interval.

20. A non-transitory, computer-readable medium storing a set of instructions which, when executed by a control circuit of a medical device, cause the medical device to:
- deliver an electrical stimulation pulse to a patient's heart;
- schedule a next electrical stimulation pulse to be delivered at a pacing interval;
- determine a drop time interval based on the pacing interval;
- receive a cardiac electrical signal by sensing circuitry of the medical device;
- apply a cardiac event sensing threshold to the cardiac electrical signal by holding the cardiac event sensing threshold at a first threshold value starting after the electrical stimulation pulse until an expiration of the drop time interval determined based on the pacing interval; and
- sense a cardiac event attendant to a myocardial depolarization of the patient's heart in response to the cardiac electrical signal crossing the cardiac event sensing threshold.

* * * * *